(12) United States Patent
Audell et al.

(10) Patent No.: US 11,986,613 B2
(45) Date of Patent: May 21, 2024

(54) MICROSTRUCTURE SYSTEMS AND METHODS FOR PAIN TREATMENT

(71) Applicants: KitoTech Medical, Inc., Seattle, WA (US); Robert Arman Audell, Beverly Hills, CA (US)

(72) Inventors: Robert Arman Audell, Beverly Hills, CA (US); Ronald J. Berenson, Seattle, WA (US); Cheuk Yin Paul Leung, Bellevue, WA (US)

(73) Assignee: KitoTech Medical, Inc., Seattle, WA (US)

( * ) Notice: Subject to any disclaimer, the term of this patent is extended or adjusted under 35 U.S.C. 154(b) by 315 days.

(21) Appl. No.: 17/180,538

(22) Filed: Feb. 19, 2021

(65) Prior Publication Data

US 2021/0252264 A1 Aug. 19, 2021

Related U.S. Application Data

(60) Provisional application No. 62/981,376, filed on Feb. 25, 2020, provisional application No. 62/978,454, filed on Feb. 19, 2020.

(51) Int. Cl.
*A61M 37/00* (2006.01)

(52) U.S. Cl.
CPC . *A61M 37/0015* (2013.01); *A61M 2037/0023* (2013.01); *A61M 2037/0061* (2013.01);
(Continued)

(58) Field of Classification Search
CPC ...... A61M 37/0015; A61M 2037/0023; A61M 2037/0061; A61M 2205/054;
(Continued)

(56) References Cited

U.S. PATENT DOCUMENTS

| 345,541 A | 7/1886 | Reiohardt |
|---|---|---|
| 2,472,009 A | 5/1949 | Gardner |

(Continued)

FOREIGN PATENT DOCUMENTS

| AU | 767122 B2 | 10/2003 |
|---|---|---|
| AU | 2004200303 A1 | 2/2004 |

(Continued)

OTHER PUBLICATIONS

"U.S. Appl. No. 14/408,244, Examiner Interview Summary dated Nov. 8, 2018", 3 pgs.

(Continued)

*Primary Examiner* — Amber R Stiles
(74) *Attorney, Agent, or Firm* — Schwegman Lundberg & Woessner, P.A.

(57) ABSTRACT

The present invention relates generally to devices comprising one or more microstructures that are used to relieve, treat or prevent pain. The devices are designed such that they are inserted into the superficial layers of the skin to achieve pain relief. The devices are designed such that the microstructures are able to grasp and secure to the skin. The devices may consist of microstructures in arrays that are attached to a backing to enable the devices to adhere to the skin. Also provided are wound closure systems that comprise one or more microstructure devices along with other components, such as protective covers and therapeutics. A variety of packaging specifications are disclosed, as is a dispenser apparatus configured to enable simple one-handed application of the devices. Methods described herein provide for treatment of pain.

7 Claims, 11 Drawing Sheets

(52) U.S. Cl.
CPC . *A61M 2205/054* (2013.01); *A61M 2205/058* (2013.01); *A61M 2205/36* (2013.01); *A61M 2210/04* (2013.01)

(58) Field of Classification Search
CPC ........ A61M 2205/058; A61M 2205/36; A61M 2210/04; A61M 2037/0046; A61N 1/36021
See application file for complete search history.

(56) References Cited

U.S. PATENT DOCUMENTS

| | | |
|---|---|---|
| 2,575,205 A | 11/1951 | Brown |
| 2,619,084 A | 11/1952 | Brown |
| 2,669,747 A | 2/1954 | Detaranto |
| 3,068,869 A | 12/1962 | Hunter |
| 3,473,528 A | 10/1969 | Mishkin et al. |
| 3,613,679 A | 10/1971 | Bijou |
| 3,926,193 A | 12/1975 | Hasson |
| 3,931,821 A | 1/1976 | Kletschka et al. |
| 4,430,998 A | 2/1984 | Harvey et al. |
| 4,535,772 A | 8/1985 | Sheehan |
| 4,637,380 A | 1/1987 | Orejola |
| 4,762,260 A | 8/1988 | Richards et al. |
| 4,803,078 A | 2/1989 | Sakai |
| 5,047,047 A | 9/1991 | Yoon |
| 5,234,462 A | 8/1993 | Pavletic |
| 5,531,790 A | 7/1996 | Frechet et al. |
| 5,843,123 A | 12/1998 | Brazeau |
| 5,916,224 A | 6/1999 | Esplin |
| 5,968,097 A | 10/1999 | Frechet et al. |
| 6,168,596 B1 | 1/2001 | Wellisz et al. |
| 6,254,624 B1 | 7/2001 | Oddsen et al. |
| 6,256,533 B1 | 7/2001 | Yuzhakov et al. |
| 6,312,612 B1 | 11/2001 | Sherman et al. |
| 6,334,856 B1 | 1/2002 | Allen et al. |
| 6,379,324 B1 | 4/2002 | Gartstein et al. |
| 6,451,240 B1 | 9/2002 | Sherman et al. |
| 6,471,715 B1 | 10/2002 | Weiss et al. |
| 6,471,903 B2 | 10/2002 | Sherman et al. |
| 6,503,231 B1 | 1/2003 | Prausnitz et al. |
| 6,537,264 B1 | 3/2003 | Cormier et al. |
| 6,565,532 B1 | 5/2003 | Yuzhakov et al. |
| 6,589,202 B1 | 7/2003 | Powell |
| 6,611,707 B1 | 8/2003 | Prausnitz et al. |
| 6,652,478 B1 | 11/2003 | Gartstein et al. |
| 6,712,839 B1 | 3/2004 | Loenne |
| 6,743,211 B1 | 6/2004 | Prausnitz et al. |
| 6,931,277 B1 | 8/2005 | Yuzhakov et al. |
| 6,960,193 B2 | 11/2005 | Rosenberg |
| 7,060,192 B2 | 6/2006 | Yuzhakov et al. |
| 7,144,495 B2 | 12/2006 | Teodorczyk et al. |
| 7,160,312 B2 | 1/2007 | Saadat |
| 7,172,615 B2 | 2/2007 | Morriss et al. |
| 7,226,439 B2 | 6/2007 | Prausnitz et al. |
| 7,344,499 B1 | 3/2008 | Prausnitz et al. |
| 7,416,541 B2 | 8/2008 | Yuzhakov et al. |
| 7,455,681 B2 | 11/2008 | Wilke et al. |
| 7,510,566 B2 | 3/2009 | Jacobs et al. |
| 7,626,070 B2 | 12/2009 | Propp |
| 7,658,728 B2 | 2/2010 | Yuzhakov |
| 7,683,234 B2 | 3/2010 | Gurtner et al. |
| 7,686,829 B2 | 3/2010 | Elliott et al. |
| 7,785,301 B2 | 8/2010 | Yuzhakov |
| 7,806,266 B2 | 10/2010 | Hagino et al. |
| 8,049,058 B2 | 11/2011 | Propp |
| 8,053,624 B2 | 11/2011 | Propp |
| 8,063,263 B2 | 11/2011 | Gurtner et al. |
| 8,157,839 B2 | 4/2012 | Riskin et al. |
| 8,168,850 B2 | 5/2012 | Gurtner et al. |
| 8,183,428 B2 | 5/2012 | Gurtner et al. |
| 8,250,729 B2 | 8/2012 | Lee et al. |
| 8,388,631 B2 | 3/2013 | Oostman, Jr. et al. |
| 8,389,791 B2 | 3/2013 | Gurtner et al. |
| 8,397,973 B1 | 3/2013 | Hausen |
| 8,414,548 B2 | 4/2013 | Yuzhakov |
| 8,540,672 B2 | 9/2013 | McAllister |
| 8,663,275 B2 | 3/2014 | O'Malley et al. |
| 8,777,987 B2 | 7/2014 | Herrmann et al. |
| 8,852,214 B2 | 10/2014 | Kubiak |
| 8,894,683 B2 | 11/2014 | Weadock et al. |
| 9,050,086 B2 | 6/2015 | Belson et al. |
| 9,089,328 B2 | 7/2015 | Belson et al. |
| 9,358,376 B2 | 6/2016 | Altarac |
| 9,392,965 B2 | 7/2016 | Tenney et al. |
| 9,414,840 B2 | 8/2016 | Fleischmann |
| 9,427,309 B2 | 8/2016 | Kubiak et al. |
| 9,993,620 B2 | 6/2018 | Le et al. |
| 10,219,804 B2 | 3/2019 | Linder et al. |
| 10,492,780 B2 | 12/2019 | Gross et al. |
| 10,751,050 B2 | 8/2020 | Rolandi et al. |
| 10,939,912 B2 | 3/2021 | Leung et al. |
| 2001/0051815 A1 | 12/2001 | Esplin |
| 2002/0082543 A1 | 6/2002 | Park |
| 2002/0133129 A1 | 9/2002 | Arias |
| 2002/0168290 A1 | 11/2002 | Yuzhakov |
| 2002/0193754 A1 | 12/2002 | Cho |
| 2003/0028087 A1 | 2/2003 | Yuzhakov et al. |
| 2003/0028125 A1 | 2/2003 | Yuzhakov |
| 2003/0065360 A1 | 4/2003 | Jacobs |
| 2003/0074021 A1 | 4/2003 | Morriss et al. |
| 2003/0176890 A1 | 9/2003 | Buckman et al. |
| 2003/0212344 A1 | 11/2003 | Yuzhakov |
| 2004/0010276 A1 | 1/2004 | Jacobs et al. |
| 2004/0138705 A1 | 7/2004 | Heino |
| 2004/0260340 A1 | 12/2004 | Jacobs |
| 2005/0049549 A1 | 3/2005 | Wong |
| 2005/0119694 A1 | 6/2005 | Jacobs et al. |
| 2005/0143713 A1 | 6/2005 | Delmore et al. |
| 2005/0148921 A1 | 7/2005 | Hsu |
| 2005/0197699 A1 | 9/2005 | Jacobs et al. |
| 2005/0261631 A1 | 11/2005 | Clarke et al. |
| 2005/0261632 A1* | 11/2005 | Xu .................... A61M 37/0015 604/173 |
| 2006/0058842 A1 | 3/2006 | Wilke |
| 2006/0093658 A1 | 5/2006 | Sathyan |
| 2006/0147510 A1 | 7/2006 | Galer |
| 2006/0228320 A1 | 10/2006 | Minami |
| 2007/0021779 A1 | 1/2007 | Garvin et al. |
| 2007/0060867 A1* | 3/2007 | Xu ....................... A61K 9/0021 604/171 |
| 2007/0191761 A1 | 8/2007 | Boone et al. |
| 2007/0225676 A1 | 9/2007 | Prausnitz |
| 2007/0282374 A1 | 12/2007 | Sogard et al. |
| 2007/0288040 A1 | 12/2007 | Ferree |
| 2007/0293815 A1 | 12/2007 | Chan et al. |
| 2007/0299388 A1 | 12/2007 | Chan et al. |
| 2008/0009825 A1 | 1/2008 | Ringsred et al. |
| 2008/0051723 A1 | 2/2008 | Laermer |
| 2008/0125743 A1 | 5/2008 | Yuzhakov |
| 2008/0183144 A1 | 7/2008 | Trautman |
| 2008/0195035 A1 | 8/2008 | Frederickson |
| 2008/0262543 A1 | 10/2008 | Bangera et al. |
| 2008/0275409 A1 | 11/2008 | Kane et al. |
| 2009/0099437 A1 | 4/2009 | Yuzhakov |
| 2009/0131846 A1 | 5/2009 | Gurtner |
| 2009/0216326 A1 | 8/2009 | Hirpara et al. |
| 2009/0312597 A1 | 12/2009 | Bar et al. |
| 2010/0042137 A1* | 2/2010 | Oronsky ........... A61M 37/0015 604/141 |
| 2010/0048744 A1 | 2/2010 | Park |
| 2010/0137679 A1 | 6/2010 | Lashinski et al. |
| 2010/0193997 A1 | 8/2010 | Frederickson et al. |
| 2010/0256568 A1 | 10/2010 | Frederickson et al. |
| 2010/0274283 A1 | 10/2010 | Kirsch |
| 2010/0305473 A1 | 12/2010 | Yuzhakov |
| 2010/0312191 A1 | 12/2010 | Allen et al. |
| 2011/0288565 A1 | 11/2011 | Kubiak et al. |
| 2012/0029434 A1 | 2/2012 | Kobayashi et al. |
| 2012/0046586 A1 | 2/2012 | Gurtner et al. |
| 2012/0184916 A1 | 7/2012 | Kobayashi et al. |
| 2012/0203253 A1 | 8/2012 | Kubiak |
| 2012/0221044 A1 | 8/2012 | Archibald et al. |
| 2013/0123806 A1 | 5/2013 | Howlett et al. |

(56) References Cited

U.S. PATENT DOCUMENTS

| | | |
|---|---|---|
| 2013/0218083 A1 | 8/2013 | Yuzhakov |
| 2015/0032204 A1 | 1/2015 | Johansson |
| 2015/0250476 A1 | 9/2015 | Feezor et al. |
| 2015/0305739 A1 | 10/2015 | Rolandi et al. |
| 2016/0095592 A1 | 4/2016 | Levinson et al. |
| 2016/0347810 A1 | 12/2016 | Xie et al. |
| 2017/0119371 A1 | 5/2017 | Mims et al. |
| 2017/0333039 A1* | 11/2017 | Leung .................. A61B 17/064 |
| 2019/0232058 A1 | 8/2019 | Rooney et al. |
| 2021/0212686 A1 | 7/2021 | Leung et al. |
| 2021/0251628 A1 | 8/2021 | Leung et al. |
| 2023/0255630 A1 | 8/2023 | Leung et al. |

FOREIGN PATENT DOCUMENTS

| | | |
|---|---|---|
| AU | 2013273965 A1 | 12/2014 |
| AU | 2013273965 B2 | 11/2017 |
| CA | 2510389 A1 | 12/1999 |
| CA | 2330207 C | 8/2005 |
| CA | 2376128 C | 1/2009 |
| CA | 2875227 A1 | 12/2013 |
| CN | 108553408 A | 9/2018 |
| CN | 109069155 A | 12/2018 |
| EP | 0286657 A1 | 10/1988 |
| EP | 1183065 A1 | 3/2002 |
| EP | 1281352 A1 | 2/2003 |
| EP | 1284121 A2 | 2/2003 |
| EP | 1391716 A2 | 2/2004 |
| EP | 1598011 A2 | 11/2005 |
| EP | 1360931 B1 | 1/2006 |
| EP | 1360933 B1 | 7/2006 |
| EP | 1360932 B1 | 1/2007 |
| EP | 1086214 A4 | 5/2007 |
| EP | 1973479 A2 | 10/2008 |
| EP | 2209417 A1 | 7/2010 |
| EP | 1183064 B1 | 12/2012 |
| EP | 1183066 B1 | 12/2012 |
| EP | 1834589 B1 | 12/2012 |
| EP | 1904158 B1 | 7/2013 |
| EP | 2861181 A1 | 4/2015 |
| IN | 192015 A | 5/2015 |
| JP | 2003533326 A | 11/2003 |
| JP | 2009545382 A | 12/2009 |
| JP | 2013512062 A | 4/2013 |
| JP | 2013532997 A | 8/2013 |
| WO | WO-8801955 A3 | 4/1988 |
| WO | WO-0074764 A1 | 12/2000 |
| WO | WO-0074765 A1 | 12/2000 |
| WO | WO-0074766 A1 | 12/2000 |
| WO | WO-0167944 A2 | 9/2001 |
| WO | WO-0191846 A2 | 12/2001 |
| WO | WO-02072189 A2 | 9/2002 |
| WO | WO-2005123173 A1 | 12/2005 |
| WO | WO-2006016364 A2 | 2/2006 |
| WO | WO-2006124671 A2 | 11/2006 |
| WO | WO-2007002523 A2 | 1/2007 |
| WO | WO-2007081430 A2 | 7/2007 |
| WO | WO-2008019051 A2 | 2/2008 |
| WO | WO-2008020632 A1 | 2/2008 |
| WO | WO-2008067290 A2 | 6/2008 |
| WO | WO-2009048687 A1 | 4/2009 |
| WO | WO-2010124712 A1 | 11/2010 |
| WO | WO-2010140760 A2 | 12/2010 |
| WO | WO-2011016230 A1 | 2/2011 |
| WO | WO-2011067297 A1 | 6/2011 |
| WO | WO-2011135531 A2 | 11/2011 |
| WO | WO-2012170497 A2 | 12/2012 |
| WO | WO-2013042723 A1 | 3/2013 |
| WO | WO-2013096026 A1 | 6/2013 |
| WO | WO-2013188884 A1 | 12/2013 |
| WO | WO-2017151806 A1 | 9/2017 |
| WO | WO-2021168345 A1 | 8/2021 |

OTHER PUBLICATIONS

"U.S. Appl. No. 14/408,244, Final Office Action dated Mar. 6, 2019", 21 pgs.

"U.S. Appl. No. 14/408,244, Final Office Action dated Oct. 18, 2017", 21 pgs.

"U.S. Appl. No. 14/408,244, Non Final Office Action dated Feb. 7, 2017", 14 pgs.

"U.S. Appl. No. 14/408,244, Non Final Office Action dated Jun. 4, 2018", 13 pgs.

"U.S. Appl. No. 14/408,244, Non Final Office Action dated Nov. 27, 2019", 13 pgs.

"U.S. Appl. No. 14/408,244, Notice of Allowance dated Apr. 15, 2020", 10 pgs.

"U.S. Appl. No. 14/408,244, Preliminary Amendment filed Mar. 23, 2015", 5 pgs.

"U.S. Appl. No. 14/408,244, Response filed Feb. 20, 2018 to Final Office Action dated Oct. 18, 2017", 14 pgs.

"U.S. Appl. No. 14/408,244, Response filed Jul. 24, 2017 to Non Final Office Action dated Feb. 7, 2017", 11 pgs.

"U.S. Appl. No. 14/408,244, Response filed Nov. 5, 2018 to Non Final Office Action dated Jun. 4, 2018", 9 pgs.

"U.S. Appl. No. 14/408,244, Response to Final Office Action dated Mar. 6, 2019 filed Jun. 6, 2019", 14 pgs.

"U.S. Appl. No. 15/446,999, Examiner Interview Summary dated Mar. 9, 2020", 4 pgs.

"U.S. Appl. No. 15/446,999, Examiner Interview Summary dated Sep. 29, 2020", 3 pgs.

"U.S. Appl. No. 15/446,999, Final Office Action dated Jul. 12, 2019", 15 pgs.

"U.S. Appl. No. 15/446,999, Final Office Action dated Aug. 10, 2020", 15 pgs.

"U.S. Appl. No. 15/446,999, Non Final Office Action dated Mar. 8, 2019", 14 pgs.

"U.S. Appl. No. 15/446,999, Non Final Office Action dated Apr. 7, 2020", 18 pgs.

"U.S. Appl. No. 15/446,999, Non Final Office Action dated Dec. 20, 2019", 21 pgs.

"U.S. Appl. No. 15/446,999, Notice of Allowance dated Nov. 17, 2020", 11 pgs.

"U.S. Appl. No. 15/446,999, PTO Response to Rule 312 Communication dated Feb. 17, 2021", 2 pgs.

"U.S. Appl. No. 15/446,999, Response filed Mar. 20, 2020 to Non Final Office Action dated Dec. 20, 2019", 23 pgs.

"U.S. Appl. No. 15/446,999, Response filed Jun. 10, 2019 to Non Final Office Action dated Mar. 8, 2019", 15 pgs.

"U.S. Appl. No. 15/446,999, Response filed Jul. 24, 2020 to Non Final Office Action dated Apr. 7, 2020", 21 pgs.

"U.S. Appl. No. 15/446,999, Response filed Oct. 12, 2020 to Final Office Action dated Aug. 10, 2020", 18 pgs.

"U.S. Appl. No. 15/446,999, Response filed Nov. 12, 2019 to Final Office Action dated Jul. 12, 2019", 19 pgs.

"U.S. Appl. No. 15/446,999, Response to Restriction Requirement dated Jun. 18, 2018 filed Nov. 2, 2018", 8 pgs.

"U.S. Appl. No. 15/446,999, Restriction Requirement dated Jun. 18, 2018", 9 pgs.

"U.S. Appl. No. 17/249,083, Non Final Office Action dated Jul. 25, 2022", 15 pgs.

"U.S. Appl. No. 17/249,083, Preliminary Amendment filed Mar. 9, 2021", 3 pgs.

"Australian Application Serial No. 2013273965, Amendment filed Nov. 6, 2017", 5 pgs.

"Australian Application Serial No. 2013273965, Examination Report dated Jun. 1, 2017", 4 pgs.

"Australian Application Serial No. 2013273965, Examination Report dated Nov. 7, 2016", 3 pgs.

"Australian Application Serial No. 2013273965, Response filed Mar. 20, 2017 to Examination Report dated Nov. 7, 2016", 15 pgs.

"Australian Application Serial No. 2013273965, Response filed Nov. 2, 2017 to Examination Report dated Jun. 1, 2017", 15 pgs.

"Canadian Application Serial No. 2,875,227, Office Action dated Jun. 23, 2020", 3 pgs.

"Canadian Application Serial No. 2,875,227, Office Action dated Nov. 18, 2019", 4 pgs.

(56) References Cited

OTHER PUBLICATIONS

"Canadian Application Serial No. 2,875,227, Response filed Mar. 18, 2020 to Office Action dated Nov. 18, 2019", 26 pgs.

"Canadian Application Serial No. 2,875,227, Response filed Aug. 20, 2019 to Examiner's Rule 30(2) Requisition dated Feb. 21, 2019", 44 pgs.

"Chinese Application Serial No. 201780027281.1, Office Action dated Oct. 16, 2020", w/ English translation, 8 pgs.

"European Application Serial No. 13733182.3, Communication pursuant to Article 94(3) EPC dated Jul. 11, 2017", 5 pgs.

"European Application Serial No. 13733182.3, Communication pursuant to Article 94(3) EPC dated Sep. 2, 2016", 4 pgs.

"European Application Serial No. 13733182.3, Response filed Jan. 10, 2017 to Communication pursuant to Article 94(3) EPC dated Sep. 2, 2016", 17 pgs.

"European Application Serial No. 13733182.3, Response filed Jan. 22, 2018 to Communication pursuant to Article 94(3) EPC dated Jul. 11, 2017", 70 pgs.

"European Application Serial No. 13733182.3, Response filed Aug. 25, 2015 to Communication pursuant to Rules 161(2) and 162 EPC dated Feb. 26, 2015", 15 pgs.

"European Application Serial No. 17711444.4, Notification Regarding Rule 164 and Article 94(3) EPC dated Dec. 20, 2019", 10 pgs.

"European Application Serial No. 17711444.4, Response filed Apr. 9, 2019 to Communication Pursuant to Rules 161(1) and 162 EPC dated Oct. 16, 2018", 22 pgs.

"European Application Serial No. 17711444.4, Response filed Apr. 30, 2020 to Notification Regarding Rule 164 and Article 94(3) EPC dated Dec. 20, 2019", 57 pgs.

"European Application Serial No. 19174754.2, Extended European Search Report dated Oct. 21, 2019", 6 pgs.

"European Application Serial No. 19174754.2, Response Filed May 11, 2020 to Extended European Search Report dated Oct. 21, 2019", 8 pgs.

"Indian Application Serial No. 2939/KOLNP/2014, First Examiner Report dated Jan. 7, 2020", 5 pgs.

"International Application Serial No. PCT/US2013/046181, International Preliminary Report on Patentability dated Dec. 16, 2014", 6 pgs.

"International Application Serial No. PCT/US2013/046181, International Preliminary Report on Patentability dated Dec. 24, 2014", 7 pgs.

"International Application Serial No. PCT/US2013/046181, International Search Report dated Aug. 13, 2013", 3 pgs.

"International Application Serial No. PCT/US2013/046181, Written Opinion dated Aug 13, 2013", 5 pgs.

"International Application Serial No. PCT/US2017/020258, International Preliminary Report on Patentability dated Sep. 13, 2018", 14 pgs.

"International Application Serial No. PCT/US2017/020258, International Search Report dated Jul. 25, 2017", 6 pgs.

"International Application Serial No. PCT/US2017/020258, Written Opinion dated Jul. 25, 2017", 12 pgs.

"International Application Serial No. PCT/US2021/018901, International Preliminary Report on Patentability dated Sep. 1, 2022", 10 pgs.

"International Application Serial No. PCT/US2021/018901, International Search Report dated Apr. 22, 2021", 2 pgs.

"International Application Serial No. PCT/US2021/018901, Written Opinion dated Apr. 22, 2021", 8 pgs.

"Japanese Application Serial No. 2015-517482, Examiners Decision of Final Refusal dated Sep. 11, 2018", w/ English translation, 7 pgs.

"Japanese Application Serial No. 2015-517482, Office Action dated Mar. 10, 2020", w/ English translation, 5 pgs.

"Japanese Application Serial No. 2015-517482, Office Action dated Mar. 14, 2017", w/ English translation, 8 pgs.

"Japanese Application Serial No. 2015-517482, Response filed Jun. 4, 2020 to Office Action dated Mar. 10, 2020", w/ English claims, 8 pgs.

"Japanese Application Serial No. 2019-002286, Notification of Reasons for Refusal dated Nov. 26, 2019", w/ English translation, 10 pgs.

"Korean Application Serial No. 10-2015-7000949, Notice of Preliminary Rejection dated Feb. 27, 2020", w/ English translation, 12 pgs.

"Mexican Application Serial No. MX/a/2014/015365, Office Action dated May 7, 2019", w/ English translation, 7 pgs.

"New Zealand Application Serial No. 702677, Search Report dated Oct. 28, 2015", 2 pgs.

"Singapore Application Serial No. 11201408221Y, Written Opinion dated Jun. 29, 2016", 4 pgs.

Francesko, et al., "Chitin, Chitosan and Derivatives for Wound Healing and Tissue Engineering", Adv Biochem Engin/Biotechnol 125, Springer, (2011), 27 pgs.

Lawton, et al., "Novel Haemostatic Dressings", JR Army Med Corps, (2009), 309-314.

Lee, et al., "β-Chitin-based wound dressing containing silver sulfurdiazine", Journal of Materials Science: Materials in Medicine; 11(12): 817-823. (Abstract), (2000), 1 pg.

Mahdavi, et al., "A biodegradable and biocompatible gecko-inspired tissue adhesive", Proceedings of the National Academy of Sciences, (2008), 2307-2312.

Rajabi, Mina, et al., "Flexible and Stretchable Microneedle Patches with Integrated Rigid Stainless Steel Microneedles for Transdermal Biointerfacing", PloS one, 11(12), e0166330, (Dec. 9, 2016), 13 pgs.

Sugamori, et al., "Local herostatic effects of microcrystalline partially deacetylated chitin hydrochloride", J Biomed Mater Res 49(2), (2000), 225-232.

Yusof, et al., "Preparation and characterization of chitin beads as a wound dressing precursor", Journal of Biomedica Materials Research, 54(1), (2000), 59-68.

Zhong, et al., "A Chitin Nanofiber Ink for Airbrushing, Replica Molding, and Microcontact Printing of Self-assembled Macro-, Micro-, and Nanostructures", Adv Materials 23(41), (2011), 4776-4781.

Zhong, et al., "A facile bottom-up route to self-assembled biogenic chitin nanofibers", Soft Matter 6(21), (2010), 5298-5301.

U.S. Appl. No. 17/249,083, filed Feb. 19, 2021, Elastic and Flexible Wound Closure Device.

"U.S. Appl. No. 17/249,083, Final Office Action dated Feb. 9, 2023", 12 pgs.

"U.S. Appl. No. 17/249,083, Response filed Oct. 21, 2022 to Non Final Office Action dated Jul. 25, 2022", 10 pgs.

* cited by examiner

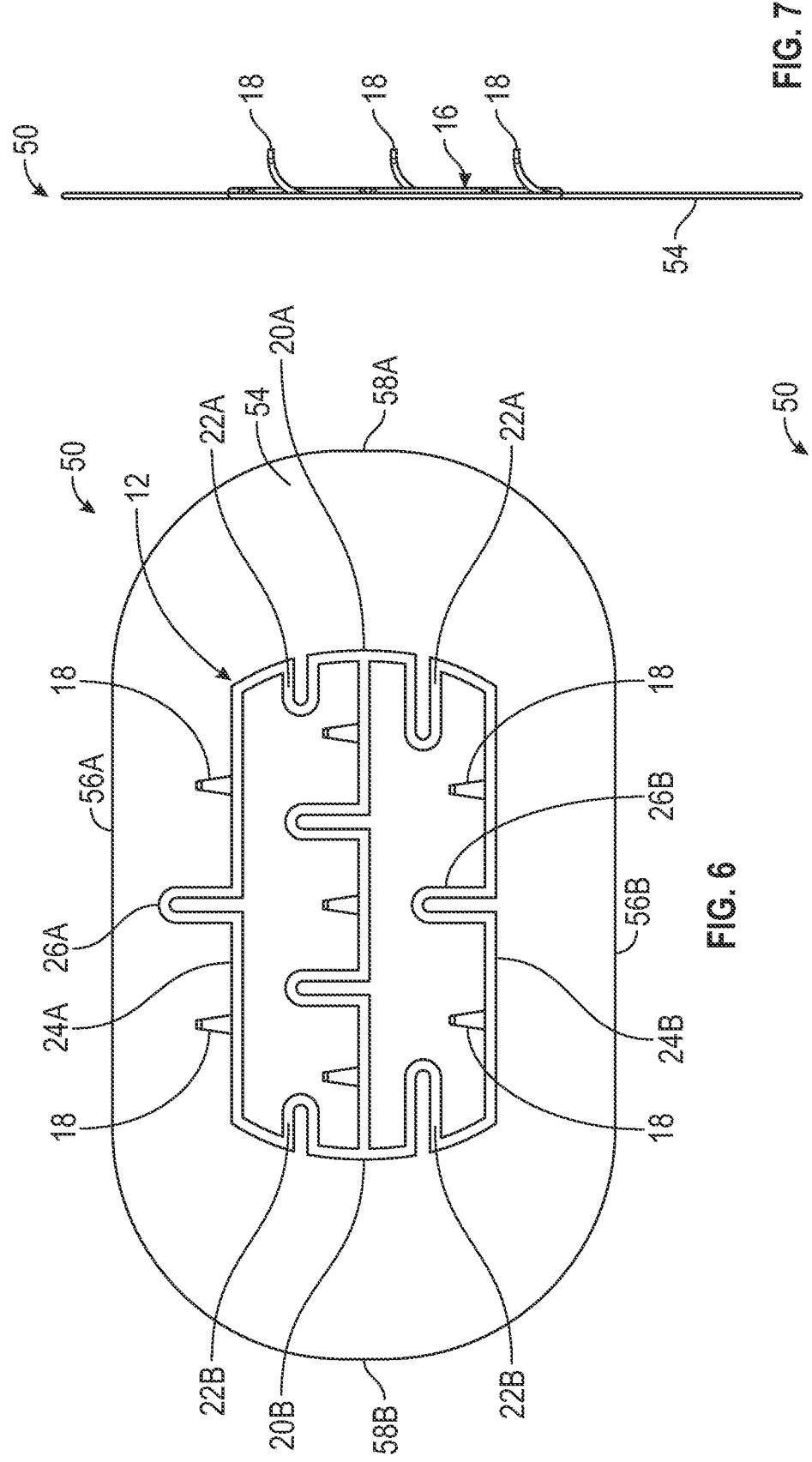

MICROSTRUCTURE SYSTEMS AND METHODS FOR PAIN TREATMENT

BACKGROUND

The treatment of pain is a major medical challenge today given that it is associated with significant disability and poor quality of life. There continues to be a need for more effective and less toxic therapeutic approaches. Although drugs such as non-steroidal anti-inflammatory drugs and opioids can be effective, they have many side effects that make them suboptimal. Physical therapy, electrical stimulation, ultrasound, massage, and other physical approaches are also used but are variably effective.

Insertion of needles into tissues has also proven effective in some conditions. There are two major approaches. In acupuncture, needles are inserted deeply in the skin (deep dermis and subcutaneous tissue) at remote sites from the source of pain. Dry needling in which needles are inserted into painful muscles is also used to alleviate pain often caused by spasms known as trigger points.

Overview

The present invention described here uses microstructures, such as microneedles or microblades, to alleviate pain. The microstructures are inserted into the superficial skin (epidermis and upper dermis) near the site of pain and are thus distinct from treatment using acupuncture or dry needling. They are also less painful upon insertion and have reduced risks compared to these other needle therapies The microstructures may be incorporated into a base that contains several microstructures (an array) or used individually. The array may be attached to a backing. The array and backing combined together produces a device in which microstructures can remain in the skin for extended periods of time (up to four weeks) to achieve more effective pain relief. The microstructures can be made of a variety of materials, different shapes, and sizes, and densities (number per $cm^2$) to provide pain relief. Pain of musculoskeletal, neuropathic, visceral, and other origin may be effectively treated with the microstructures. Pain due to trauma or inflammatory conditions can respond to treatment. Both acute and chronic pain can be relieved with the microstructure treatment.

Pain is a universal condition, which is responsible for considerable disability and reduced quality of life. It is associated with nearly all tissues and organs of the body. Pain can be either acute lasting hours to days or chronic in which the pain can occur for months to years. It can be recurrent, episodic, or sporadic with varying frequency based on the condition and patient.

Musculoskeletal pain is extremely common affecting the majority of Americans each year. It is most often caused by diseases or injury, but can also occur in the setting of overuse or reduced use of muscle. Any tissue of this system can cause pain including muscle, bone, and joints, and their associated structures, including tendons, ligaments, and bursa. In addition, internal elements such as the articular capsule and meniscus in joints and discs in between spinal vertebrae can cause pain. Pain of neuropathic origin, such as that associated with nerve damage or inflammation is often observed with degenerative disease and other injuries to the spine can result in pain. In addition, herpetic neuralgia is a common condition that occurs after infection with herpes zoster virus. Other common types of pain include headaches, such as migraines. Another type of pain is known as visceral pain, which is from organs, such as stomach, intestine, colon, lung, heart, kidneys, and bladder.

Treatment of pain is targeted to treating the underlying disorder as well as providing agents that reduce pain itself. Some of these agents act to directly reduce pain, while others reduce inflammation that often causes pain. Others act by treating both of these conditions.

Agents to treat pain can be administered by any one of a number of routes including systemic (oral, intravenous, intramuscular, subcutaneous, transdermal), or can be administered locally to the site of pain via topical or direct injection into the painful site. Sometimes, analgesia is achieved by regionally blocking a nerve or even portion of the spinal cord which is linked to the area of pain.

Agents that are used to treat pain include acetaminophen, non-steroidal anti-inflammatory drugs, corticosteroids, opioids, lidocaine, indomethacin, and colchicine, all of which can be associated with side effects and toxicities. Non-steroidal anti-inflammatory drugs' adverse effects include nausea and vomiting, gastrointestinal bleeding, heart failure, and renal insufficiency. Corticosteroids also act via their anti-inflammatory effects and are associated with hypertension, hyperglycemia, insomnia, headaches, and psychiatric disorders. Opioids are analgesics used for more severe pain and act via receptors that bind these molecules. These drugs are addictive and are a major cause of morbidity and mortality due to cardiorespiratory depression. Other agents that are primarily analgesics include acetaminophen and lidocaine. Acetaminophen has a risk of liver damage. In addition to their side effects, each of these classes of drugs has only variable and inconsistent therapeutic effects. In some cases, this may be due to tolerance that develops with repeated use, such as opioids, while in others, it is due to their relatively modest analgesic effects (e.g., acetaminophen).

Topical administration of some of these agents (primarily non-steroidal anti-inflammatory drugs and lidocaine) has been used to treat localized pain to muscles, joints, and other tissues. Most of these agents act by penetrating the target tissue to alleviate pain.

There are certain types of agents that are administered topically and do not appear to relieve pain by direct effects on the damaged tissue. Instead, they act on the skin to achieve their therapeutic effects to relieve pain originating from deeper tissues and organs. Some of these agents are known as counterirritants, and are defined by the FDA as an externally applied substance that causes irritation or mild inflammation of the skin for the purpose of relieving pain in muscles, joints and viscera distal to the site of application. They differ from the anesthetics, analgesics, and antipruritic agents, however, in that the pain relief they produce results from stimulation—rather than depression—of the cutaneous sensory receptors and occurs in structures of the body other than the skin areas to which they are applied as for example, in joints, muscles, tendons and certain viscera. Counterirritants include capsaicin, menthol, camphor, and methyl salicylate, and other natural and synthetic molecules.

Counterirritants work by stimulating (irritating) sensory nerve receptors in the skin. The irritation of these receptors in skin may also inhibit pain signals from pain receptors referred to as nociceptors thereby blocking transmission of pain sensations to the brain. The balance between nociceptive and non-nociceptive receptors in the CNS is what controls the sensation of pain. This is known as the gate control theory of pain. Counterirritants ultimately shift the balance so the threshold for pain sensitivity is increased reducing pain sensation. While the receptors that activate counterirritants are located in the skin, the neurological effects are not limited to the skin. Critical to the therapeutic effects is that sensory fibers in the skin that are stimulated by counter irritants are linked to the same nerves that innervate the painful region, whether it be muscle, joints, or other tissues. For example, a reduction of muscle tension often results from stimulation of these sensor receptors in the skin that is innervated by sensory fibers of the same segment. This may be how counterirritants relieve muscle pain.

Surprisingly, we have discovered that the insertion of short, small microstructures (approximately 1 mm in height) into the superficial skin (into the upper dermis) can lead to marked alleviation of pain due to both acute and chronic conditions. These include arthritis, sprains, myofascial trigger points as well as condition of uncertain etiology. The same modality will likely be effective in conditions associated with pain of neuropathic origin as well as those in other tissues and organs in the body. Although the exact mechanism of how the insertion of microstructures into the upper skin layers alleviates pain in deeper tissues is not known, it may act via a mechanism similar to counterirritants. Mild inflammation has been observed upon treatment with microstructures consistent with what is observed with counterirritants; however, pain is minimal in contrast to the significant pain required to achieve therapeutic effects with many counterirritants.

Importantly, the therapeutic effects are distinct from other devices that use needles to alleviate pain. Acupuncture inserts needles into the deeper layers of tissues, including subcutaneous tissues and interstitum to reduce pain at specific anatomic sites—commonly referred to as acupuncture points, or acupoints that are not typically near the location of the pain in the body. The general theory of acupuncture is based on the premise that there are patterns of energy flow (Qi) through the body that are essential for health. Disruptions of this flow are believed to be responsible for disease. Acupuncture may, it has been theorized, correct imbalances of flow at identifiable points close to the skin. In contrast to the technology described in this patent application, acupuncture requires long needles that measure from about 8 to 130 mm in length to achieve their therapeutic effects. Studies comparing shorter (4 mm) and longer needles (8 mm) demonstrated that the shorter needles had minimal analgesic effects. Dry needling is the method in which needles are inserted directly into muscles that cause pain. The method requires the direct insertion of the needles into the painful tissue to produce therapeutic effects. In contrast, in the technology of the present invention, the microstructures are inserted in the superficial skin near the underlying deeper tissue, such as muscle, joint, or tendon, where the pain originates from to provide pain relief. The microstructure treatment is safer reducing risks of infections and bleeding and also less painful than acupuncture or dry needling because the microstructures only penetrate the upper skin layer.

In an example, a device to reduce or prevent pain or inflammation can comprise one or more microstructures.

In an additional example, a method of reducing or preventing pain or inflammation can comprise applying a microstructure device to tissue, penetrating a microstructure of the microstructure device into the tissue, and treating or preventing pain with the microstructure.

BRIEF DESCRIPTION OF THE DRAWINGS

FIG. 6 is a plan view of the microstructure-based device of FIG. 5.

FIG. 7 is a first side view of the microstructure-based device of FIG. 6.

FIG. 8 is a second side view of the microstructure-based device of FIG. 6.

DETAILED DESCRIPTION

Definitions and Abbreviations

Figure 1:
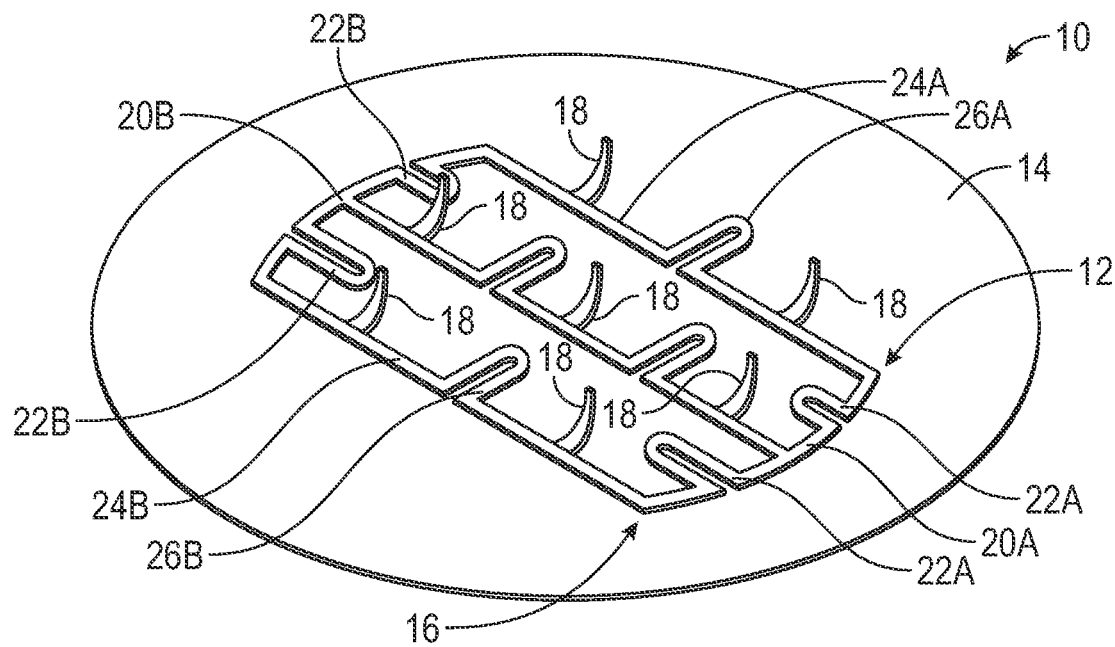
FIG. 1 is a perspective view of a first example of a microstructure-based device used to treat pain.

The terminology used herein is for the purpose of describing particular embodiments or examples only, and is not intended to limit the scope of the present invention, which will be limited only by the appended claims. Unless defined otherwise, all technical and scientific terms used herein have the same meaning as commonly understood by one of ordinary skill in the art to which this invention belongs. As used in the specification and appended claims, unless specified to the contrary, the following terms have the meaning indicated.

As used herein and unless otherwise indicated, the terms "a" and "an" are taken to mean "one", "at least one" or "one or more". Unless otherwise required by context, singular terms used herein shall include pluralities and plural terms shall include the singular.

Reference to the term "e.g." is intended to mean "e.g., but not limited to" and thus it should be understood that whatever follows is merely an example of a particular embodiment, but should in no way be construed as being a limiting example. Unless otherwise indicated, use of "e.g." is intended to explicitly indicate that other embodiments have been contemplated and are encompassed by the present invention.

By "about" is meant a quantity, level, value, number, frequency, percentage, dimension, size, amount, weight or length that varies by as much as 30, 25, 20, 15, 10, 9, 8, 7, 6, 5, 4, 3, 2 or 1% to a reference quantity, level, value, number, frequency, percentage, dimension, size, amount, weight or length. In any embodiment discussed in the context of a numerical value used in conjunction with the term "about." it is specifically contemplated that the term about can be omitted.

Unless the context requires otherwise, throughout the present specification and claims, the word "comprise" and variations thereof, such as, "comprises" and "comprising" are to be construed in an open, inclusive sense, that is as "including, but not limited to".

By "consisting of" is meant including, and limited to, whatever follows the phrase "consisting of." Thus, the phrase "consisting of" indicates that the listed elements are required or mandatory, and that no other elements may be present.

By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

Reference throughout this specification to "one embodiment" or "an embodiment" or "some embodiments" or "certain embodiments" mean that a particular feature, structure or characteristic described in connection with the embodiment is included in at least one embodiment of the present invention. Thus, the appearances of the phrases "in one embodiment" or "in an embodiment" or "in certain embodiments" in various places throughout this specification are not necessarily all referring to the same embodiment. Furthermore, the particular features, structures, or characteristics may be combined in any suitable manner in one or more embodiments. Additionally, an "embodiment" can be synonymous with an example of a particular feature, structure, characteristic or device of the present disclosure.

"Optional" or "optionally" means that the subsequently described event of circumstances may or may not occur, and that the description includes instances where said event or circumstance occurs and instances in which it does not.

"Substantially" or "essentially" means nearly totally or completely, for instance, 95% or greater of some given quantity.

As used herein, the term "device" as used generally means a device used for reducing pain or inflammation.

As used herein, the term "tissue" means any human or other animal tissue including, but not limited to skin, muscle, tendon, bone, heart, lung, kidney, brain, bowel, colon, rectum, stomach, esophagus, etc.

Reference to the term "PMMA" as used herein is meant to refer to poly(methyl methacrylate), which is also known as Poly(methyl 2-methylpropenoate (IUPAC name), polymethyl methacrylate, or more commonly known as Plexiglass™.

The terms "affixed" and "attached" are used interchangeably throughout, and have their ordinary meaning, e.g., being connected or fastened to something else. Accordingly, other terms such as "connected", "fastened", and "bound" may also be used in a similar manner.

The term "grasp" or "grasping" is used herein, to describe a microstructure-based anchoring of a closure device to its intended location on the surface of the skin or tissue to which it is applied; said anchoring not requiring penetration into the skin or tissue by the microstructures, but instead e.g., being anchored via friction generated by the contact of the microstructures with the skin or tissue. In some embodiments, the device is anchored by grasping, optionally with or without the assistance of the other various components of the present devices and systems. e.g., a protective cover or adhesive.

The term "penetration" or "penetrate" is meant herein to refer to the action of piercing the skin or tissue, e.g., with one or more of the microstructures disclosed herein.

The term "inflammation" is meant to have its ordinary medical meaning. i.e. a biological response of a tissue to a harmful stimulus. Common signs of inflammation include pain, heat, redness (erythema), swelling (edema), and loss of function.

The term "base" is meant generally to describe a supporting means from which one or more microstructures protrude. In some embodiments, the base comprises a plurality of microstructures; and in other embodiments devices comprising singular microstructures on a base are provided. The base may be a separate component upon which one or more microstructures are affixed; or alternatively, the microstructures and the base may be one continuous component that are fabricated at the same time, optionally from the same or different materials. For example, but not to be limited in any way, some embodiments of the present invention provide for devices comprising one or more microstructure arrays patterned on a base, wherein both the base and the microstructures are made out of polymethylmethacrylate (PMMA). In examples, the microstructures can be made out of metal, such as stainless steel. e.g., 316 stainless steel. In one such embodiment, the microstructures are manufactured using a replica molding technique, wherein both the microstructures and the array are manufactured simultaneously, and are thus in essence one single component. Further embodiments provide for a variety of base specifications including. e.g., thickness, length, width, and composition. In certain embodiments, the base comprises a substantially planar upper surface and a substantially planar lower surface; said upper surface comprising one or more microstructures, and said lower surface optionally being affixed to a backing. In such an embodiment, the upper surface comprising the microstructures is intended to be put in contact with the skin or tissue of the patient and the lower surface is intended to be exposed to the external environment, or optionally to be in contact with a protective cover, e.g., a cover comprising adhesive.

The terms "array" and "microstructure array" are used herein to describe a two-dimensional configuration of two or more microstructures on a "base", as described herein, said base having a substantially planar upper surface from which the microstructures protrude. The "array" may be in any suitable shape or pattern, and the array may be of any suitable size or dimensions. Furthermore, arrays may comprise any suitable number or density of microstructures, said microstructures optionally extending from the base at angle, or in a substantially perpendicular manner.

An "array region" as used herein is meant to describe an area of the present devices upon which one or more microstructure arrays are affixed. Accordingly, in some embodiments the array region is a portion of the backing upon which one or more bases are affixed, said bases each comprising one or more microstructure or microstructure arrays. In some particular embodiments, the devices of the present invention comprise at least two "array regions" that are separated from one another by an isthmus, as described herein.

The term "isthmus" as used herein refers to a space with no arrays, that separates two or more microstructure "arrays" or "array regions". "Isthmus separation" refers to the distance separating two arrays on opposing sides of an isthmus. The isthmus may comprise any suitable material, and may in some embodiments be rigid, flexible, and/or stretchable. The size and shape of the isthmus may vary, and in some embodiments the device will comprise an isthmus and a backing, both being made out of the same material, while in other embodiments the material comprised in the isthmus will differ from that of the backing. In certain embodiments, the isthmus is simply created by affixing two or more microstructure arrays upon a backing such that a space separates the two arrays. In still other embodiments, the isthmus is a portion of a base comprising a plurality of microstructure arrays (i.e., the isthmus and the microstructures are made of the same material). Non-limiting examples of two different types of isthmuses can be seen in FIGS. 24 and 10 wherein the shape, composition (silicone vs. thermoplastic polyurethane ("TPU")), and properties (i.e. stretchable vs. non-stretchable) have been varied. In some embodiments, the isthmus ranges from 1 mm in length to 15 mm in length. Accordingly, in these embodiments, the devices of the present invention may comprise isthmuses that are 1 mm in length, or they may comprise isthmuses that are 2 mm; 3 mm; 4 mm; 5 mm; 6 mm; 7 mm; 8 mm; 9 mm; 10 mm; 11 mm; 12 mm; 13 mm; 14 mm; or 15 mm in length, including all decimals (e.g., 1.5 mm, 1.6 mm, 1.7 mm, etc.) and ranges (e.g., 1-15 mm, 5-10 mm, 10-15 mm, 3-4 mm, 5-6 mm, 6-8 mm, etc.) in between, of the isthmus lengths set forth herein. The width of the isthmus may vary. In some embodiments the isthmus width is the same as the base or backing of the device. In other embodiments, the isthmus is wider or narrower than the base or backing of the device. Thus, the width of the isthmus may range from as small as 1 mm to as large as 50 cm or more. A bridge may also be considered as an isthmus in various configurations.

Accordingly, isthmus widths may range from approximately 1 mm, 2 mm, 3 mm, 4 mm, 5 mm, 6 mm, 7 mm, 8 mm, 9 mm, 1 cm, 2 cm, 3 cm, 4 cm, 5 cm, 10 cm, 20 cm, 30 cm 40 cm 50 cm or longer, including all integers (e.g., 11 mm, 12 mm 13 mm, etc.) and ranges (e.g., 2 mm-50 cm, 5 mm-15 mm, 5 mm-10 mm, etc.) in between of the isthmus widths set forth herein.

As used herein, when components are said to be positioned or distributed "anisotropically" it is meant that the components are not uniform throughout, but instead their properties vary directionally. Thus, e.g., in some embodiments, anisotropic positioning refers to variation in the components of individual microstructures comprised in a microstructure array, said microstructures comprising directional variability in their physical properties, e.g., their aspect ratios or angles of attachment to a backing. In other embodiments, this variability may be in regard to directional differences between different arrays. Anisotropic variability may be in one direction, or in more than one direction.

As used herein, the term "microstructure" refers to a three-dimensional structure projecting from or connected to a base. A microstructure may be an integral part of the base (i.e., the microstructure and base are monolithic). Alternatively, the microstructure may be of separate construction than the base but be joined to the base (e.g., through adhesive, bonding, etc.).

Microstructures typically have dimensions on the micron size scale, although certain dimensions may extend into the millimeter size scale (e.g., length or height) and certain dimensions may be smaller than one micron (e.g., nano scale tip width). Representative microstructures include microneedles, microblades, microanchors, microfishscale, micropillars, and microhairs.

A microstructure includes a foundation, a tip, and a body joining the foundation with the tip.

As used herein, the term "foundation" refers to the two-dimensional area where the base meets the microstructure. The foundation can be any two-dimensional shape, including a circle, oval, ellipse, triangle, rectangle, square, quadrilateral, or higher-order polygon.

As used herein, the term "tip" refers to the end of the microstructure distal to the foundation and base. The tip may be a single point (e.g., a needle), a line (e.g., a blade), or other shape.

As used herein, the term "body" refers to the portion of the microstructure between the foundation and the tip. The body may also be referred to herein as a "shaft" of the microstructure. The body has a "length" that is equal to the longest distance connecting a point on the foundation to the tip.

The microstructure can be either straight or curved. In certain embodiments, the body connects the foundation to the tip without curvature along its length. In other embodiments, the body is curved along its length between the foundation and the tip.

As used herein, the term "straight" refers to a microstructure having no curvature (i.e., no concave or convex surfaces) along the body between the foundation and the tip. As used herein, the term "curved" refers to a microstructure having one or more concave or convex surfaces along the body between the foundation and the tip.

Straight and curved microstructures can be defined in terms of a "face angle" (OF), which is the smallest angle formed between the base and the microstructure. The face angle will always be greater than the structure angle.

As used herein, the term "articulated" refers to a microstructure that does not curve continuously but instead curves via one or more joints connecting straight portions. An articulated microstructure may also be referred to as "beveled."

As used herein, the term "convex" refers to a microstructure having at least one line along the outer surface of the body that deviates outwardly from a straight line between the foundation and the tip.

As used herein, the term "concave" refers to a microstructure having at least one line along the outer surface of the body that deviates inwardly from a straight line between the foundation and the tip.

As used herein, the term "angled" refers to a microstructure that is not perpendicular to the base. The angle of a microstructure in relation to the base can be understood with reference to The "center point" is the center of the foundation. The angle ("center point angle"; $\theta c$) formed between the line and the base defines the angle of the entire microstructure. For microstructures, if the tip is not directly above the center point then the microstructure is angled.

Curved microstructures may be defined by an angle if a tip-to-center point line can be drawn so as to define an angle in relation to the base. However, extensively curved microstructures may not allow a straight line to be drawn through the body from the tip to the center point. As used herein, the term "microneedle" is intended to refer to any microstructure comprising straight or tapered shafts. In one embodiment, the diameter of the microneedle is greatest at the base end of the microneedle and tapers to a point at the end distal the base. The microneedle can also be fabricated to have a shaft that includes both a straight (untapered) portion and a tapered portion. The microneedles can be formed with shafts that have a circular cross-section in the perpendicular, or the cross-section can be non-circular. For example, the cross-section of the microneedle can be polygonal (e.g. star-shaped, square, rectangular, and triangular), oblong, or another shape. The tip portion of the microneedles can have a variety of configurations. The tips can be symmetrical or asymmetrical about the longitudinal axis of the microneedle shaft. In one embodiment, the tips are beveled. In another embodiment, the tip portion is tapered. In one embodiment, the tapered tip portion is in the shape of a pyramid on a shaft portion having a square cross-section, such that the microneedle is in the shape of an obelisk. Of course, the tip and/or shaft can be rounded, or have another shape, as well. In some embodiments the microneedles comprise a shape that is a e.g., rod, cone, square, rectangle, pyramid, cylinder.

As used herein, the term "microblade" is intended to refer to a needle-like microstructure comprising a tip that is not a point, but is instead a blade. The tip portion of these structures is wide in a first dimension (50 µm in this picture) and very narrow in a second dimension, with respect to the first dimension (e.g., less than 10 µm in this picture) Furthermore, in some embodiments, the thickness at the tip is smaller than the width of the microblades near their base.

As used herein, the term "microanchor" is intended to refer to any microstructure capable of anchoring a device according to the present disclosure to skin or tissue. Examples of microanchors include microstructures with ends shaped like hooks or barbs. As used herein, the term "barb" refers to a tip configuration comprising angled portions projecting away from the tip in order to secure the barb within the penetrated skin or tissue.

As used herein, the term "microfishscale" is intended to refer to any microstructure comprising a scale that partially overlaps, with other scales of microscale dimensions and mimics the scale of a fish.

As used herein, the term "micropillar" is intended to refer to any microstructure comprising a cylindrical shape.

As used herein, the term "microhair" is intended to refer to any microstructure comprising hair-like features which enable the contacting and sticking of the microhair to another object via van der Waals forces.

As used herein, the term "Microstaple" is intended to refer to the product, microMend®, which is manufactured by KitoTech Medical (Seattle, Wash.).

As used herein, the term "microMend" refers to the wound closure product designated MM12MP2 (12 packages of multipack of 2 MP devices per package in a box), MM12MP4 (12 packages of multipack of 4 MP devices per package in a box). MM12SM2 (12 packages of multipack of 2 SMALL devices per package in a box). MM12SM4 (12 packages of multipack of 4 SMALL devices per package in a box), MM12XS2 (12 packages of multipack of 2 EXTRA SMALL devices per package in a box), MM12W2S (12 packages of multipack of 2 WIDE-S devices per package in a box), MM12W2A (12 packages of multipack of 2 WIDE-A devices per package in a box). MM12LG2 (12 packages of multipack of 2 LARGE devices per package in a box). MM12S2S (Wide-s, 12 packs of 2) or SU2 (Umbilical device, pack of 2), which are manufactured by KitoTech Medical (Seattle, Wash.). Information on the product can be found at the website: www.micromendskinclosure.com.

Any suitable Microstaple or other microstructure device may be used such as described in International Application No. PCT/US2013/046181, entitled "Microstructure-based wound closure devices," filed on Jun. 16, 2013 and described in U.S. Patent Application No. 20170333039, entitled "MICROSTRUCTURE-BASED SYSTEMS. APPARATUS, AND METHODS FOR WOUND CLOSURE," filed on Mar. 1, 2017, which are incorporated herein by reference in their entirety.

As used herein, the term "patch" refers to a piece of material that is worn on the skin or other tissue.

The term "tapered" is meant to describe a microstructure wherein the width or diameter gradually diminishes along the length of the needle from the base to the tip, such that the base comprises the largest width or diameter, and the tip comprises the smallest width or diameter. A "partially tapered" microstructure is one in which a portion of the microstructure is tapered and a portion of the microstructure is not tapered. For example, but not to be limited, such a microstructure can comprise a tapered portion extending from a block shaped base; or e.g., a cylindrical base portion can extend toward the tip for a certain length, and then a tapered portion can continue to the tip. Alternatively, the microstructure can comprise a tapered portion extending from the base, with a non-tapered portion being at the tip end of the microstructure.

The term "stretchable" as used herein is meant to encompass any material that can be elongated in any direction. e.g., as a result of a pulling force. "Stretchable" encompasses the term "elastic" and thus an object that is said to be stretchable should be understood to optionally comprise elasticity. Thus in some embodiments, if an object is said to be stretched, this is meant to include at least two embodiments; the first being that the stretching force will be counteracted by a retractile force, and thus once the stretching force is removed, the object will inherently attempt to retract (e.g., as is the case with an elastic object). The second embodiment is one in which the object does not inherently comprise elasticity, and thus no such retractile force is inherent.

The term "flexible" is meant to describe any material that is capable of sustaining a bending force without being damaged. In some embodiments, a "flexible" material comprises enough flexibility as to allow the device of the present invention to bend so as to fit the contours of the biological barrier, such as, e.g., the skin, vessel walls, or the eye, to which the device is applied.

The term "backing" as used herein, is meant to describe an optional component of the present devices which is attached to one or more arrays. In some embodiments the backing attaches two or more microstructure arrays together. As is thoroughly described in the detailed description, the backing may comprise any suitable material, and in several embodiments, it is flexible, stretchable, elastic, or combinations thereof.

The term "cover" as used herein in meant to describe an optional component of the systems disclosed herein whereby it covers the device. After application of the devices of the present invention, such a cover may be optionally applied over and/or attached to the top of the device, e.g., assist in securing the device in place. The covers may be made of any suitable material, as is discussed and defined thoroughly in the detailed description section below. In some embodiments the covers comprise adhesive.

When it is said that one or more microstructures are "affixed to a backing" it is meant that the microstructures may optionally be either directly affixed to the backing, or indirectly affixed to the backing (e.g., in some embodiments, "affixed to a backing" is meant to encompass the scenario wherein the microstructures are fashioned on, or affixed to, a base, said base being affixed to a backing). Accordingly, the phrase "one or more microstructures affixed to a backing" can appropriately be used interchangeably with the phrase "a backing comprising one or more microstructures."

As used herein, the term "pitch" is meant to describe the distance between the tips of two or more adjacent microstructures in a given array, or in two or more separate arrays. In some embodiments the pitch ranges from 30 μm to 1 cm or more. Accordingly, certain embodiments provide for microstructure arrays as disclosed herein, wherein the microstructures are separated from one another with a pitch of 30 μm, 50 μm, 70 μm, 90 μm, 100 μm, 150 μm, 200 μm, 250 μm, 300 μm, 350 μm, 400 μm, 450 μm, 500 μm, 550 μm, 600 μm, 650 μm, 700 μm, 750 μm, 800 μm, 850 μm, 900 μm, 950 μm, 1 mm, 1.1 mm, 1.2 mm, 1.3 mm, 1.4 mm, 1.5 mm, 2 mm, 2.5 mm, 3 mm, 3.5 mm, 4 mm, 4.5 mm, 5 mm, 6 mm, 7 mm, 8 mm, 9 mm, 10 mm, or more, including all decimals (e.g., 3.1 mm, 3.2 mm, 3.3 mm, etc.) and ranges (e.g., 1-10 mm, 5-10 mm, 7-10 mm, etc.) in between, of the microstructure array pitches set forth herein. The pitch may be constant throughout an array, e.g., an equal distance separates all microstructure tips from one another in a given array; or the pitch may vary.

Reference herein to the term "tape" or "microstructure tape" or "microstructure array tape", is simply meant to describe an adhesive-comprising microstructure array roll bandage, as described herein.

The term "applicator" as used herein is meant to describe any machine or instrument that is used to affix a device, e.g., to the skin, or the use of medical instruments such as forceps, tweezers, clamps, pins, etc. to apply such a device would be considered to be use of an applicator. The term "applicator" also refers to the roll on hand-held dispenser disclosed herein. Thus, when it is said that the device is applied without an applicator, this is to be understood as being applied by human hand, without the aid of a machine or instrument.

DETAILED DESCRIPTION OF ILLUSTRATED EXAMPLES

FIG. 1 is a perspective view of microstructure device 10 used to treat pain. Microstructure device 10 can comprise microstructure array 12 and elastic backing 14. Microstructure array 12 can comprise foundation 16 and microstructures 18. Foundation 16 can comprise arcuate sidewalls, or struts, 20A and 20B having spring structures 22A and 22B, respectively, and straight sidewalls, or struts. 24A and 24B having spring structures 26A and 26B, respectively.

Figure 5:
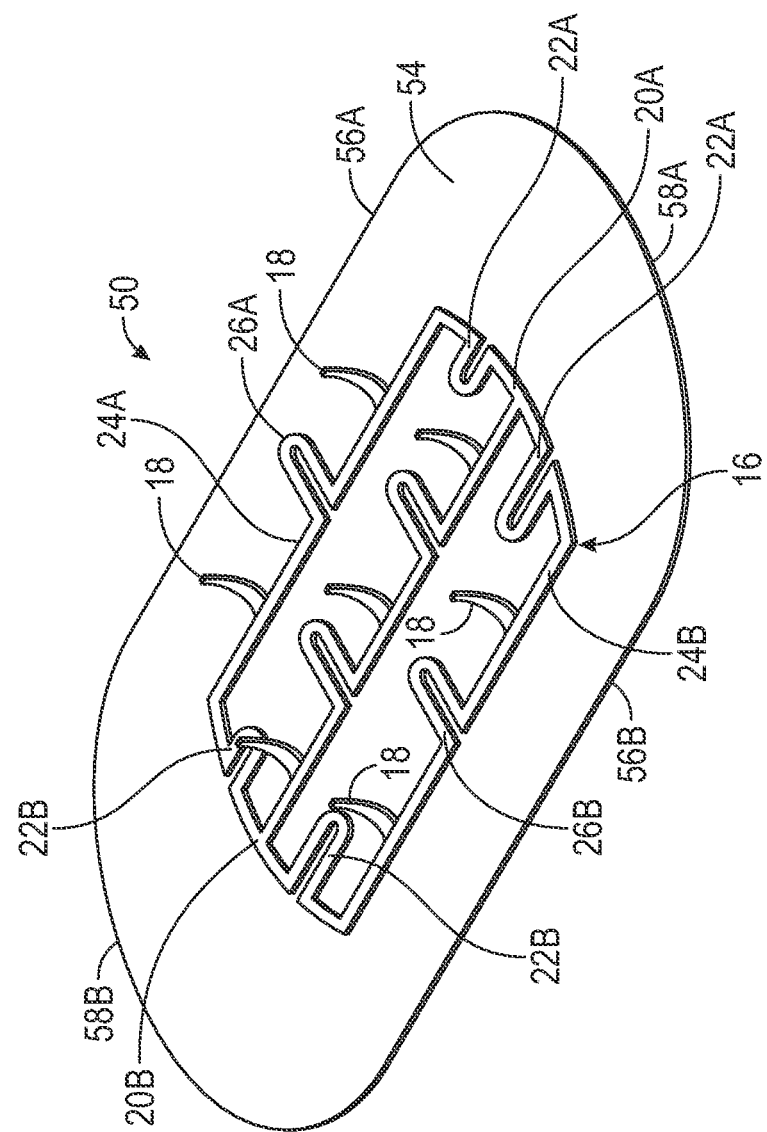
FIG. 5 is a perspective view of a second example of a microstructure-based device used to treat pain.

Backing 14 can comprise a continuous material that can be positioned adjacent tissue. Backing 14 can have any shape suitable for attaching microstructure array 12 to tissue. Thus, backing 14 can generally surround microstructure array 12. In the illustrated example, backing 14 has a circular shape. However, backing 14 can have other shapes. Backing 14 can have any shape including, but not limited to, rectangular, rectilinear, square, circular, oval, oblong and the like. For example, FIGS. 5-8 show backing 54 having an oblong shape, such as a rectangle with rounded corners. As shown in FIG. 5, backing 14 and foundation 16 can have the same or similar outer perimeter shape.

Backing 14 can comprise a stretchable/elastic substrate or base upon which other components of microstructure device 10 can be affixed. Backing 14 can comprise a sheet configured to stretch when subject to a tensile load but that will return to its original shape (or close to it) when loading is removed. In an example, backing 14 can be elastic. e.g., a substance or object able to resume its normal shape spontaneously after contraction, dilatation, or distortion.) During use applied to skin, backing 14 may be unstretched, partially stretched or completely stretched.

Backing 14 can be any material such as a fabric or polymer. In some examples, backing 14 can comprise a material singularly, or in combination, selected from the group consisting of medical tape, white cloth tape, surgical tape, tan cloth medical tape, silk surgical tape, clear tape, hypoallergenic tape, silicone, elastic silicone, polyurethane, elastic polyurethane, polyethylene, elastic polyethylene, rubber, latex, expanded PTFE (ePTFE), plastic and plastic components, polymers, biopolymers, and natural materials. In examples, backing 14 can comprise a silicone sheet. In examples, devices of the present disclosure can include bases, backings or substrates made in similar to those structures disclosed in US Patent Publication Nos. 2015/0305739 and 2017/0333039. Backing 14 can comprise a waterproof or impermeable material to prevent fluid from passing therethrough.

Backing 14 can be provided with an adhesive layer (not visible in FIG. 1) or an adhesive backing can be disposed on the tissue-facing side to allow microstructure array 12 to be secured to backing 14 and to facilitate attachment of backing 14 to tissue, along with microstructure array 12. The adhesive can be applied uniformly across the entire backing or only around the perimeter of the backing (e.g., backing 14) to ensure good adhesion and sealing to a tissue area or interspersed throughout the backing. For example, the adhesive layer can comprise only a ring or loop positioned to surround foundation 16. Other adhesive patterns can also be used in this application. The terms adhesive, adhesive layer and adhesive backing are used interchangeably. Microstructure array 12 can be applied to the tissue-facing side against the adhesive layer. The adhesive can include any medical grade adhesive, such as, for example, an acrylate hydrocolloid or silicone.

Figure 2:
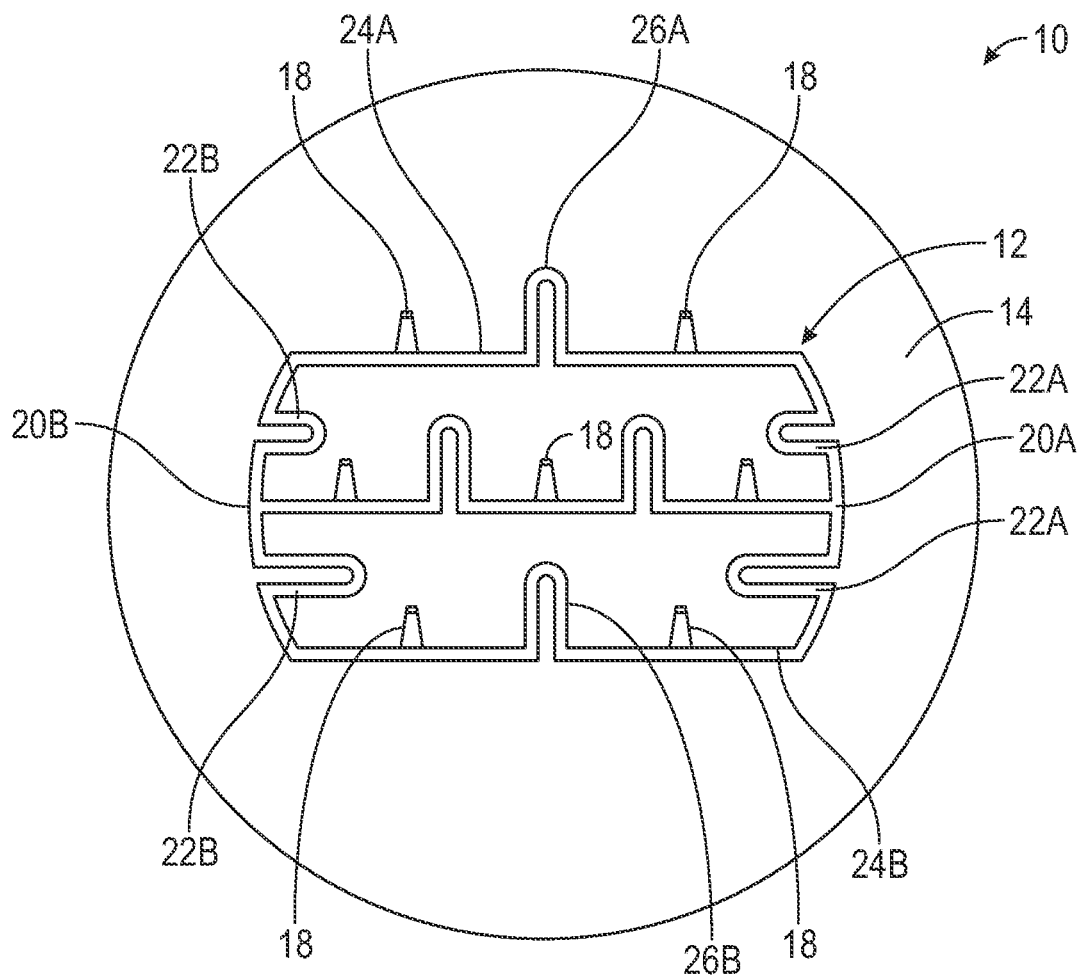
FIG. 2 is a plan view of the microstructure-based device of FIG. 1.
Figure 4:
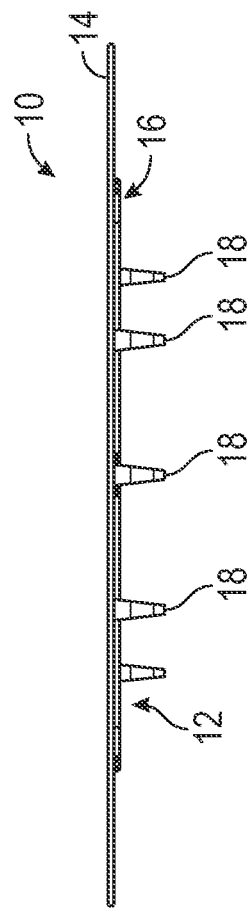
FIG. 4 is a second side view of the microstructure-based device of FIG. 2.
Figure 3:
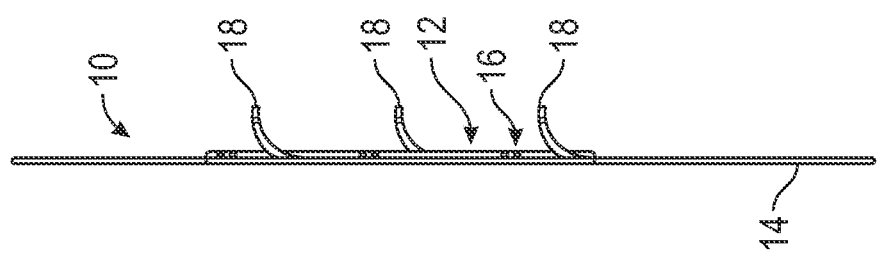
FIG. 3 is a first side view of the microstructure-based device of FIG. 2.

FIG. 2 is a bottom view microstructure device 10 of FIG. 1 showing microstructure array 12 and backing 14. FIG. 3 is a side view of microstructure device 10 of FIG. 2 showing microstructure array 12 attached to a skin-facing side of backing 14 opposite an air-facing side of backing 14. FIG. 4 is a second side view of the microstructure-based device 10 of FIG. 2 showing microstructure array 12 attached to a skin-facing side of backing 14 opposite an air-facing side of backing 14.

As can be seen in FIGS. 3 and 4, microstructure array 12 can be attached to the skin-facing side of backing 14. Microstructure array 12 can comprise foundation 16 and microstructures 18 protruding from foundation 16. In the illustrated example, microstructures 18 can be at an angle of approximately 45 degrees relative to backing 14. In examples, microstructures 18 can be perpendicular to backing 14 or less than a 90-degree angle with respect to backing 14.

As can be seen in FIG. 2, the undulations formed by spring structures 22A, 22B, 26A and 26B can provide microstructure array 12 with a spring characteristic that allows microstructure array 12 to stretch and bend. For example, the perimeter of foundation 16 can contract and expand. In examples, foundation 16 can be replaced with a plurality of foundations, each having short segments with one or more of microstructures 18.

A plurality of microstructures 18 can be provided on foundation 16. A plurality of microstructures 18 can define an array. Microstructures 18 can have a pointed tip. Microstructures 18 can comprise any micro-sized structure suitable for grabbing onto or piercing into tissue, e.g., skin, such as barbs, hooks, anchors, needles, blades, fishscales, pillars, hairs (i.e., a microstaple, a microbarb, a microneedle, a microblade, a microanchor, a microhook, a microfishscale, a micropillar, and a microhair) and the like. In an example, microstructure array 12 can be replaced by one or more microstructure arrays described in US Patent Publication Nos. 2015/0305739 and 2017/0333039. In examples, microstructure array 12 can be replaced by one or more microstructure arrays or microstructures described herein.

Microstructures 18 can be inserted into tissue to provide treatment and therapy as described herein, such as to alleviate or prevent pain.

FIG. 5 is a perspective view of microstructure device 50 used to treat pain. FIG. 6 is a plan view of the microstructure device 50 of FIG. 5. FIG. 7 is a first side view of microstructure device 50 of FIG. 6. FIG. 8 is a second side view of microstructure device 50 of FIG. 6. FIGS. 5-8 are discussed concurrently. Microstructure device 50 can comprise microstructure array 12 of FIGS. 1-4 and backing 54. Backing 54 can be configured similarly as backing 14 of FIGS. 1-4 except for shape. Backing 54 can comprise an oblong shape tracks the general shape of foundation 16. Edge 56A of backing 54 can be straight and can extend generally parallel to sidewall 24A and edge 56B of backing 54 can be straight and can extend generally parallel to sidewall 24B. Edge 58A can be curved and can curve around sidewall 20A and edge 58B can be curved and can curve around sidewall 20B.

Microstructure devices of the present disclosure can thus incorporate backings of different geometries to allow microstructure array 12 to be better fit to differently shaped anatomy of a patient, e.g., a knee, an elbow or a back.

Figure 9:
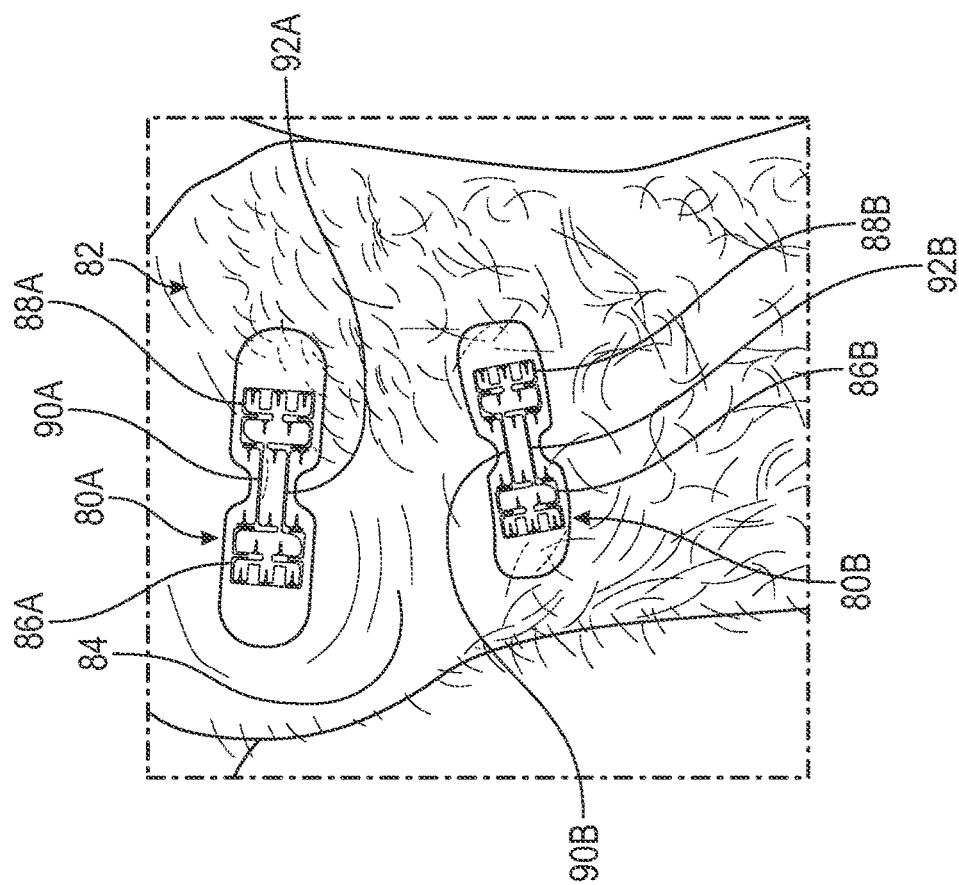
FIGS. 9 and 10 show two microstructure-based devices of the present disclosure applied over a knee area for treatment of pain.
Figure 10:
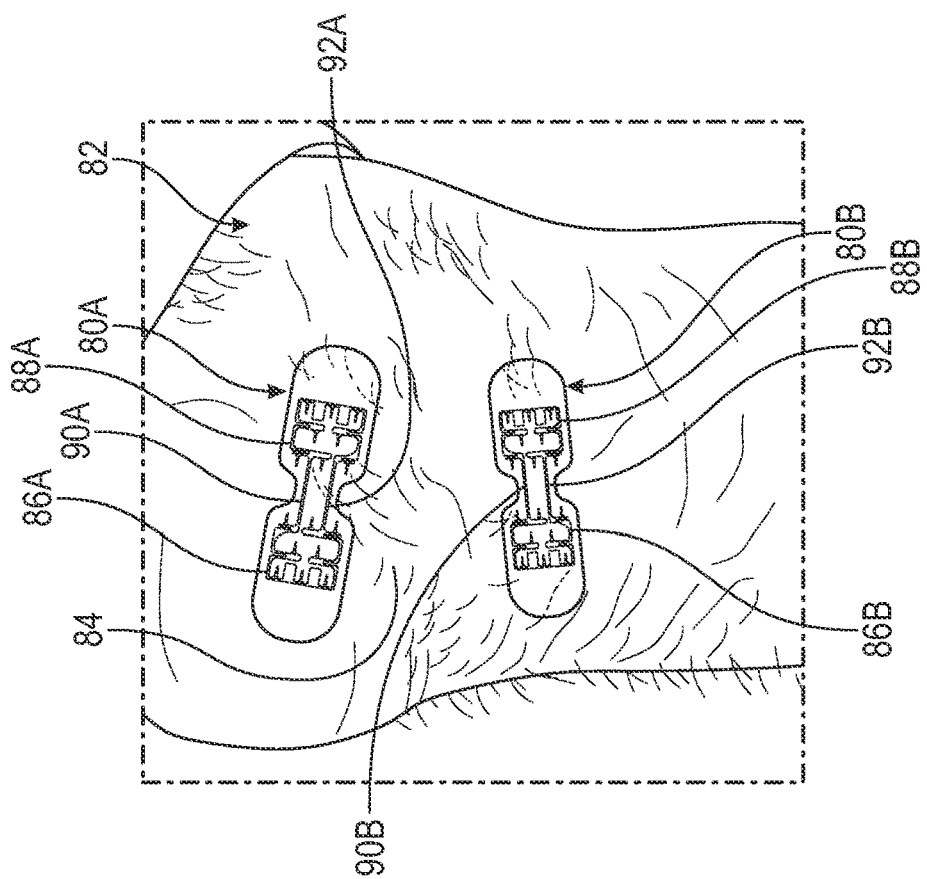

FIGS. 9 and 10 show microstructure devices 80A and 80B of the present disclosure applied to knee 82 for treatment of pain. FIGS. 9 and 10 are discussed concurrently. Microstructure device 80A can be applied superior of patella 84 and microstructure device 80B can be applied distal to patella 84 when the knee joint is in extension. In the illustrated example, microstructure devices 80A and 80B are positioned proximate the medial collateral ligament, though they can additionally be placed proximate the lateral collateral ligament or other anatomy of knee 82. Microstructure device 80A can comprise microstructure arrays 86A and 88A connected by bridges 90A and 92A. Microstructure device 80B can comprise microstructure arrays 86B and 88B connected by bridges 90B and 92B. Microstructure arrays 86A and 86B can comprise 6-microstructure arrays, e.g., microstructure arrays incorporating six microstructures for inserting into tissue, as described herein. In the illustrated example, microstructure devices 80A and 80B comprise microMend devices. Microstructure devices 80A and 80B can comprise devices as described in U.S. Patent Application No. 20170333039, entitled "MICROSTRUCTURE-BASED SYSTEMS, APPARATUS. AND METHODS FOR WOUND CLOSURE," filed on Mar. 1, 2017. As discussed below, application of microstructure devices 80A and 80B were successful in treating knee pain. Other microstructure devices described herein can also be used to treat or prevent knee pain.

Figure 11:
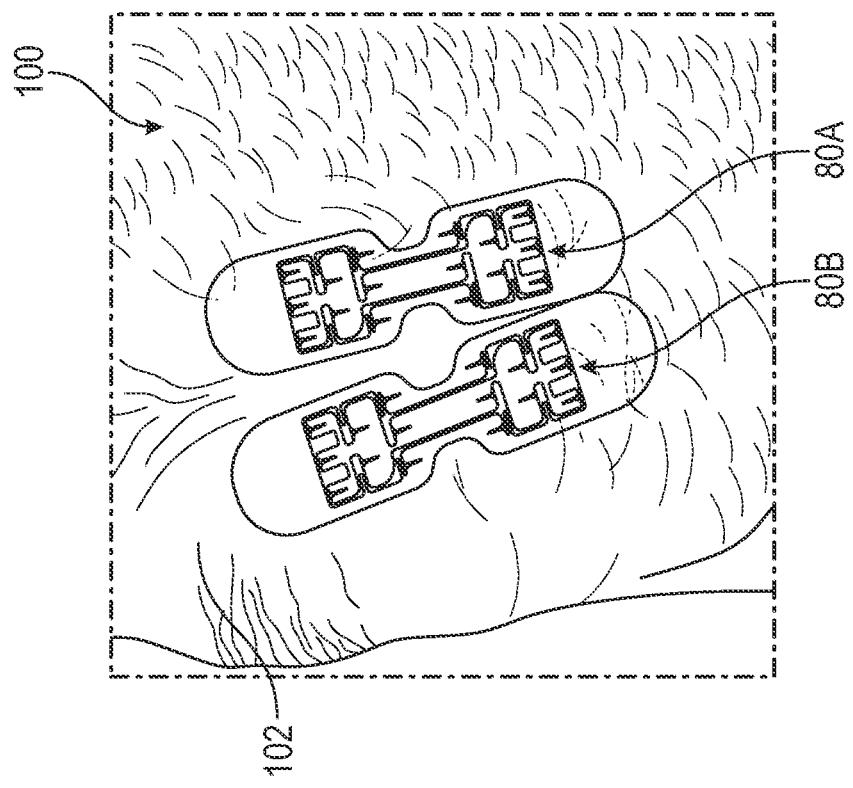
FIGS. 11 and 12 show two microstructure-based devices of the present disclosure applied over an elbow area for treatment of pain.
Figure 12:
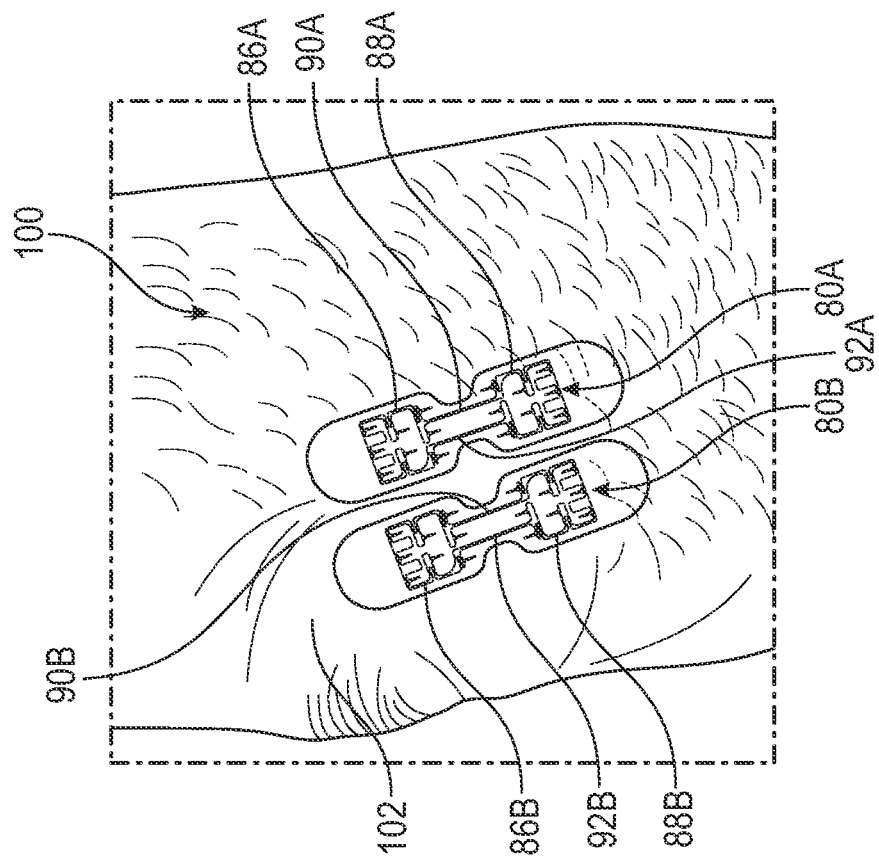

FIGS. 11 and 12 show microstructure-based devices 80A and 80B of the present disclosure applied to elbow 100 for treatment of pain. FIGS. 11 and 12 are discussed concurrently. Microstructure device 80A can be applied laterally of olecranon 102 proximate the radial collateral ligament when the elbow joint is in extension, though microstructure device 80A can be placed proximate other anatomy of elbow 100. Microstructure device 80B can be applied proximate microstructure device 80A. Microstructure device 80A can comprise microstructure arrays 86A and 88A connected by bridges 90A and 92A. Microstructure device 80B can comprise microstructure arrays 86B and 88B connected by bridges 90B and 92B. Microstructure arrays 86A and 86B can comprise 6-microstructure arrays, e.g., microstructure arrays incorporating six microstructures for inserting into tissue, as described herein. In the illustrated example, microstructure devices 80A and 80B comprise microMend devices. Microstructure devices 80A and 80B can comprise devices as described in U.S. Patent Application No. 20170333039, entitled "MICROSTRUCTURE-BASED SYSTEMS, APPARATUS. AND METHODS FOR WOUND CLOSURE." filed on Mar. 1, 2017. As discussed below, application of microstructure devices 80A and 80B were successful in treating elbow pain. Other microstructure devices described herein can also be used to treat or prevent elbow pain.

Figure 13:
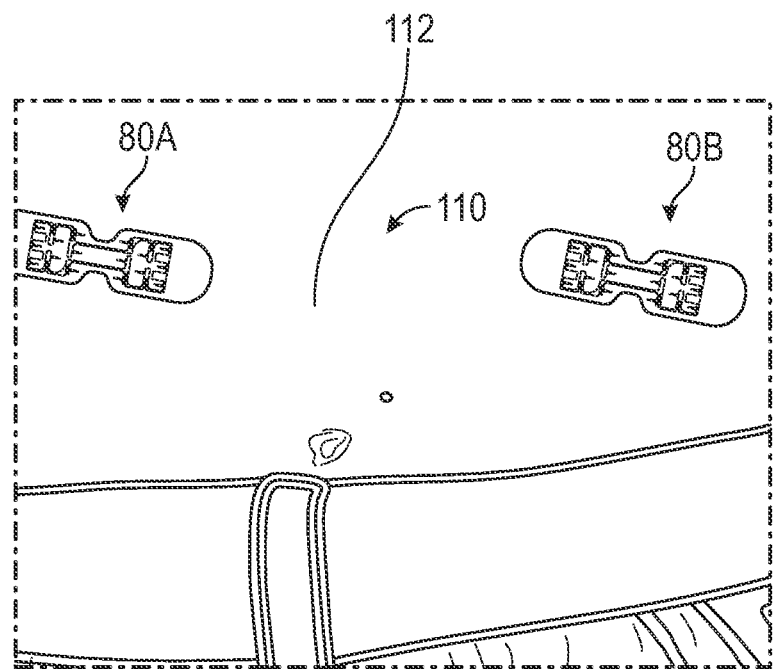
FIGS. 13 and 14 show two microstructure-based devices of the present disclosure applied over a lower back area for treatment of pain.
Figure 14:
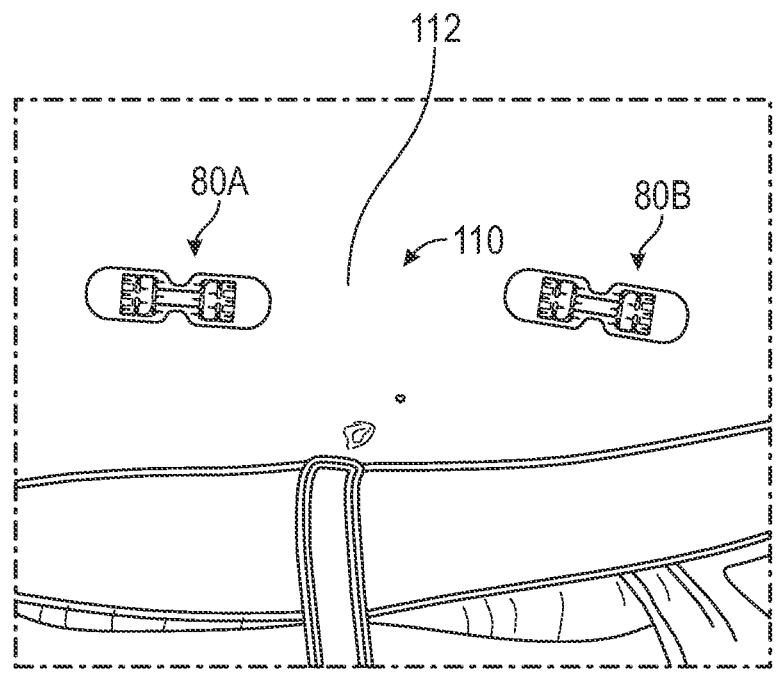

FIGS. 13 and 14 show microstructure devices 80A and 80B of the present disclosure applied to lower back area 110 for treatment of pain. Microstructure device 80A can be applied laterally of spine area 112 along a thoracolumbar fascia muscle and microstructure device 80B can be applied laterally of spine area 112 along a thoracolumbar fascia muscle opposite microstructure device 80A. Microstructure device 80A can comprise microstructure arrays 86A and 88A connected by bridges 90A and 92A. Microstructure device 80B can comprise microstructure arrays 86B and 88B connected by bridges 90B and 92B. Microstructure arrays 86A and 86B can comprise 6-microstructure arrays, e.g., microstructure arrays incorporating six microstructures for inserting into tissue, as described herein. In the illustrated example, microstructure devices 80A and 80B comprise microMend devices. Microstructure devices 80A and 80B can comprise devices as described in U.S. Patent Application No. 20170333039, entitled "MICROSTRUCTURE-BASED SYSTEMS, APPARATUS, AND METHODS FOR WOUND CLOSURE." filed on Mar. 1, 2017. As discussed below, application of microstructure devices 80A and 80B were successful in treating lower back. Other microstructure devices described herein can also be used to treat or prevent lower back pain and pain elsewhere in the back.

Figure 15:
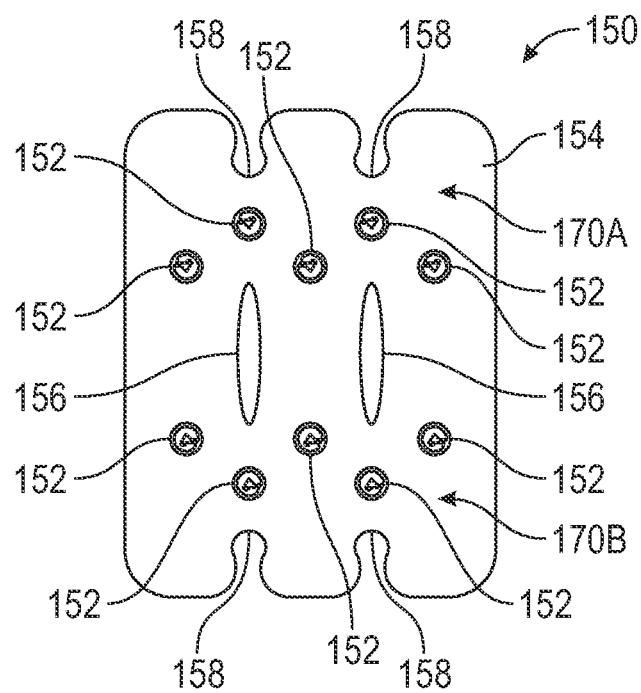
FIG. 15 is a plan view of a wide microstructure device having a plurality if individual microstructures that can be used to treat pain arranged in staggered lines.
Figure 16:
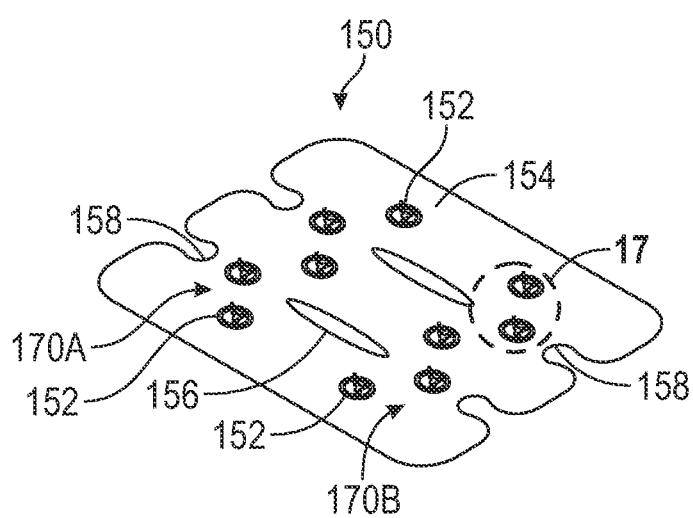
FIG. 16 is a perspective view of the wide microstructure device of FIG. 15.
Figure 17:
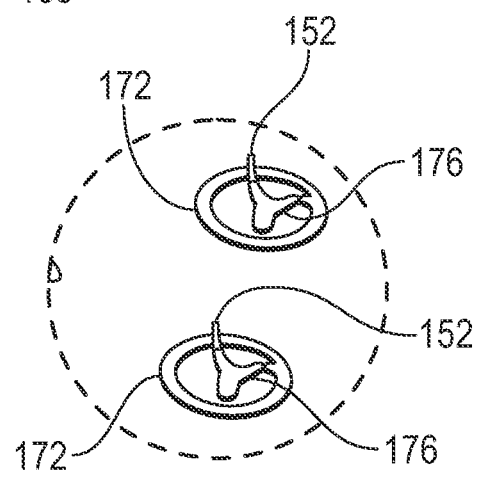
FIG. 17 is a closeup view of an individual microstructure of the wide microstructure device of FIG. 16.

FIG. 15 is a plan view of a wide microstructure device 150 having a plurality if individual microstructures 152 that can be used to treat pain arranged in staggered lines. FIG. 16 is a perspective view of wide microstructure device 150 of FIG. 15. FIG. 17 is a closeup view of microstructure 152 of the wide microstructure device of FIG. 16. FIGS. 15-17 are discussed concurrently.

FIG. 15 shows microstructure device 150 that has backing 154 that is generally the same as backings described herein, such as backings 14 and 54. Backing 154 may be a polymer or other material that is resilient and stretchable. Backing 154 can be generally flat and planar and may have an adhesive layer on the skin contacting side. The corners of backing 154 may be rounded in order to break the edges so they are less likely to catch on clothing or other object and peel away from the skin.

Optional slits or slots 156 may be disposed anywhere on the device to facilitate drainage or breathing of the skin. Slots 156 are elliptical in shape and are generally oriented so that the longitudinal axis of slot 156 extends between rows of microstructures 152. Slots 156 or slits may be any of shapes or orientations, such as rectangular, square, oval, elliptical, circular, round, etc. and combinations thereof.

Microstructure device 150 may also optionally include any of slots 158 disposed in the upper and lower edges of the device. This is not intended to be limiting and slots 158 may be disposed on any edge of device 150. Slots 158 allow backing 154 to flex and conform to the patient where the anatomy is not flat, or where the anatomy moves, thereby helping to reduce the possibility that the device will peel away and separate from the patient. The shape of slots 158 may be any shape, such as rectangular, square, oval, elliptical, circular, round, etc. and combinations thereof. Slots 156 and 158 can facilitate usage of device 150 in areas where treatment or prevention of pain is desirable.

In the example of FIGS. 15-17, microstructure device 150 is coupled to the skin of a patient with individual microstructures 152 or microstaples that are coupled to the adhesive layer on the skin contacting surface of backing 154. Here, there are two rows 170A and 170B of microstructures 152 on either side of slots 156. Each of rows 170A and 170B has at least one microstructure. In the illustrated example rows 170A and 170B each include two sub-rows of two and three microstructures 152, respectively, separated by a gap to form a single staggered row. The rows 170A and 170B may be staggered relative to one another or they may be in phase with one another. Microstructures 152 or microstaples may be any of the microstructures of microstaples disclosed herein. Therefore, the array of microstructures is a plurality of unconnected, discrete or independent microstructures.

FIG. 17 shows a close up view of microstructures 152 from device 150 in FIG. 16. Here, the microstructure includes base 172 which in this example is an annular base that can adhere to the adhesive on the skin facing surface of backing 154. Annular base 172 has arm 176 that extends radially inward from the perimeter of the annular base and microstructure 152 or microstaple is coupled to the arm and extends upward and away from arm 176 in the direction of the skin, away from the adhesive side of backing 154. Thus, the microstructures are independent and discrete from one another and may be uncoupled to one another. The microstructures generally have a tissue piercing end that is configured to be disposed in tissue deep enough to anchor the device to the patient but without causing excessive irritation, pain, redness, inflammation, bleeding. Microstructure 152 can comprise a microstructure as described herein that has a sharpened point to penetrate tissue. Prong 206 can comprise any micro-sized structure suitable for grabbing onto or piercing into tissue, e.g., skin, such as barbs, hooks, anchors, needles, blades, fishscales, pillars, hairs (i.e., a microstaple, a microbarb, a microneedle, a microblade, a microanchor, a microhook, a microfishscale, a micropillar, and a microhair) and the like.

Figure 18:
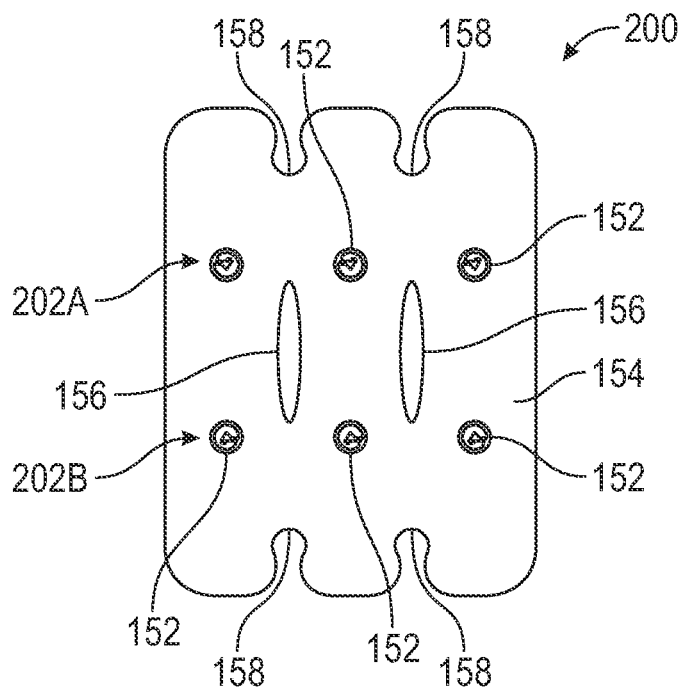
FIG. 18-20 are plan, perspective and closeup views of another configuration of a wide microstructure device having a plurality of individual microstructures arranged in straight lines.
Figure 19:
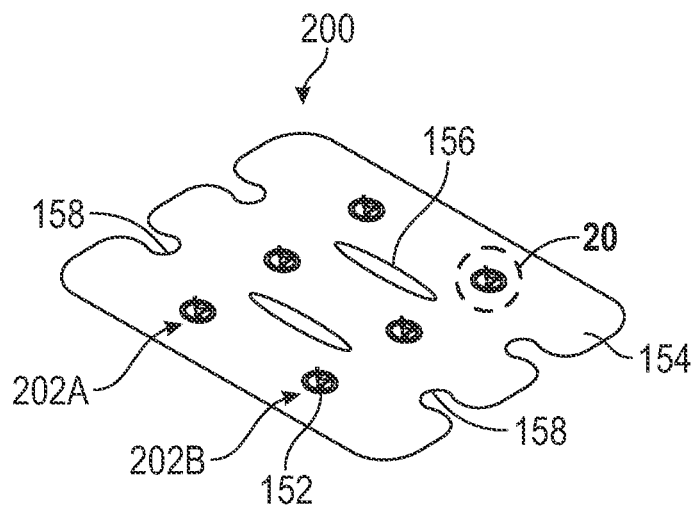
Figure 20:
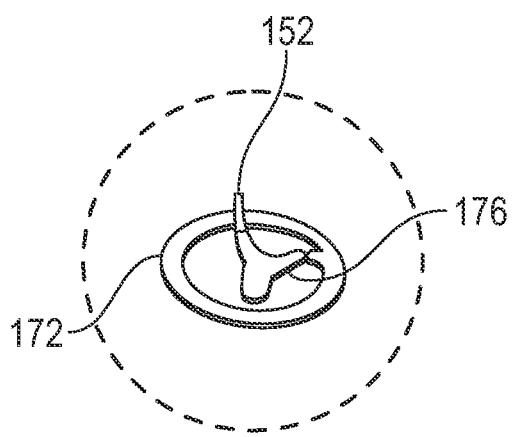

FIG. 18-20 are plan, perspective and closeup views of wide microstructure device 200 having a plurality of individual microstructures 152 arranged in straight lines. Microstructure device 200 is similar to the example in FIGS. 15-17 with the major difference being the pattern of microstructures 152 or microstaples used to secure the device to the patient's skin. Microstructures 152 are uncoupled to one another, therefore there are arrays of microstructures but the individual microstructures remain discrete and independent of one another. Rows 170A and 170B of microstructure device 150 can be replaced with rows 202A and 202B. Rows 202A and 202B can extend in straight lines, e.g., not be staggered. In the illustrated example, rows 202A and 202B include three of microstructures 152. Thus, relative to microstructure device 150 of FIGS. 15-17, the outermost microstructures 152 are eliminated to leave only the microstructures 152 closest to slots 156.

Figure 22:
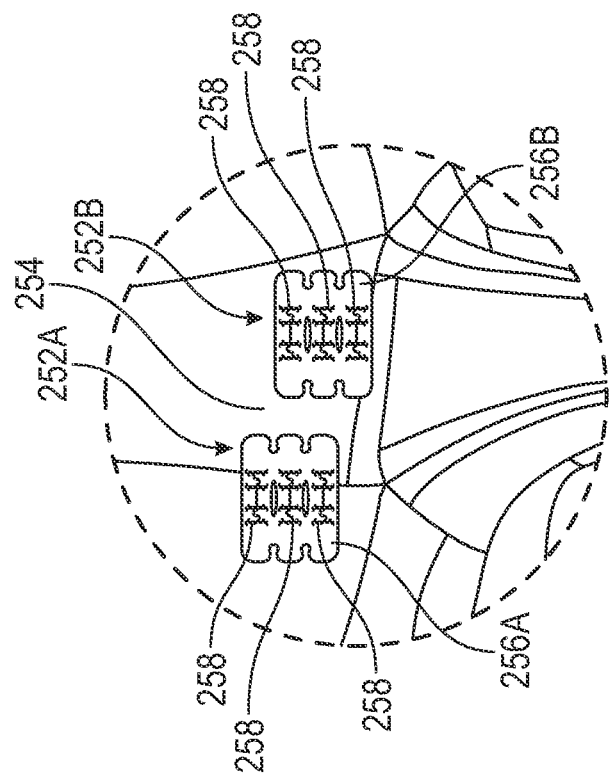
FIG. 22 is a closeup view of the pair of microstructure devices of FIG. 21.
Figure 21:
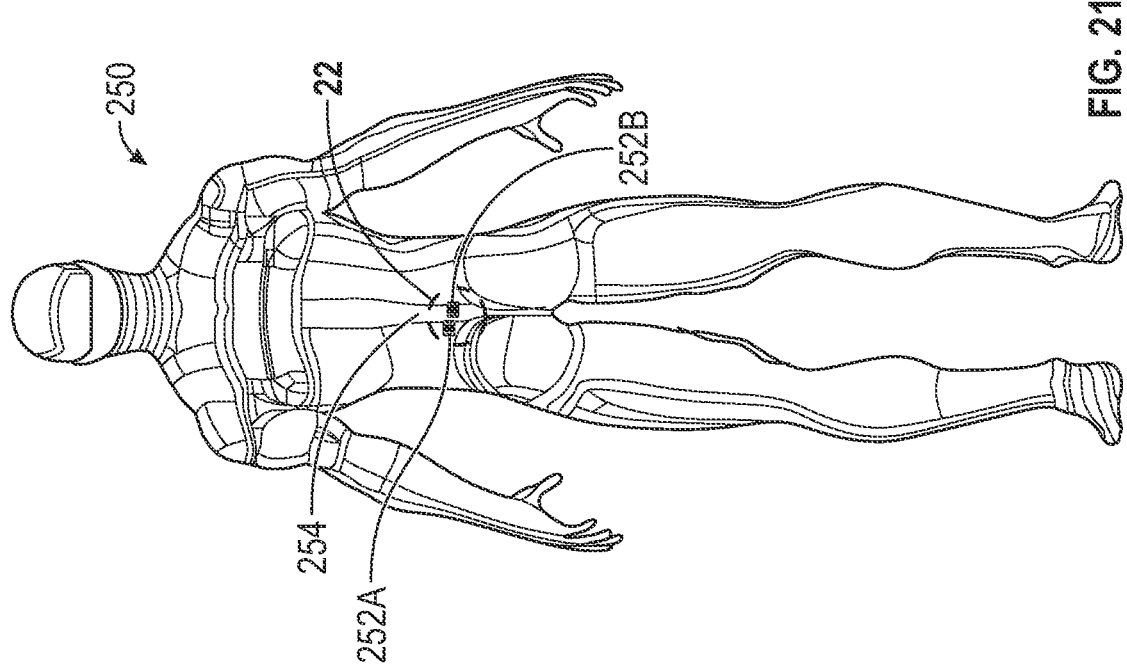
FIG. 21 is a posterior view of a human body having a pair of microstructure devices applied to a lower back area for treatment of pain.

FIG. 21 is a posterior view of human body 250 having microstructure devices 252A and 252B applied to lower back area 254 for treatment of pain. FIG. 22 is a closeup view of microstructure devices 252A and 252B of FIG. 21 shown attached to lower back area 254.

Microstructure devices 252A and 252B can comprise backings 256A and 256B, respectively. Backings 256A and 256B can be configured similarly to backing 154 of FIGS. 15 and 16. Microstructure arrays 258 can be attached to backings 256A and 256B. Microstructure arrays 258 can comprise eight microstructures, as is described with reference to FIG. 24.

Figure 23:
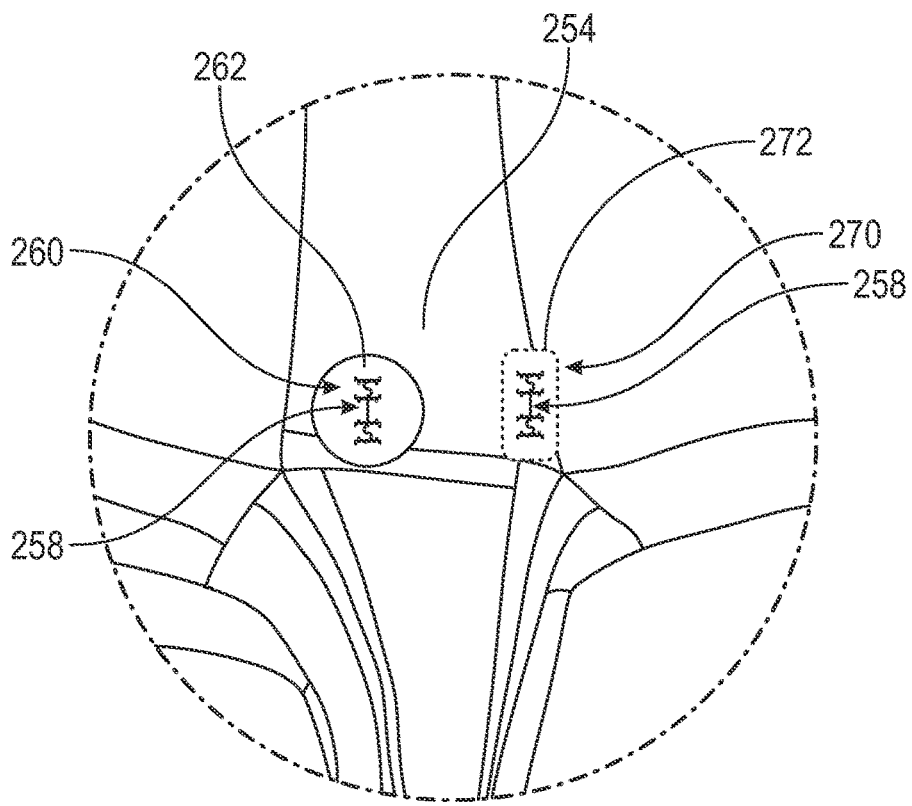
FIG. 23 is a closeup view of a pair of microstructure devices applied to a lower back area for the treatment of pain.

FIG. 23 is a closeup view of microstructure devices 260 and 270 applied to lower back area 254 for the treatment of pain. Microstructure device 260 can include backing 262. Microstructure device 270 can include backing 272. Microstructure devices 260 and 270 can comprise microstructure arrays 258. Backing 262 can be configured similarly to backing 14 of FIGS. 1 and 2. Backing 272 can be configured similarly to backing 54 of FIGS. 5 and 6.

Figure 24:
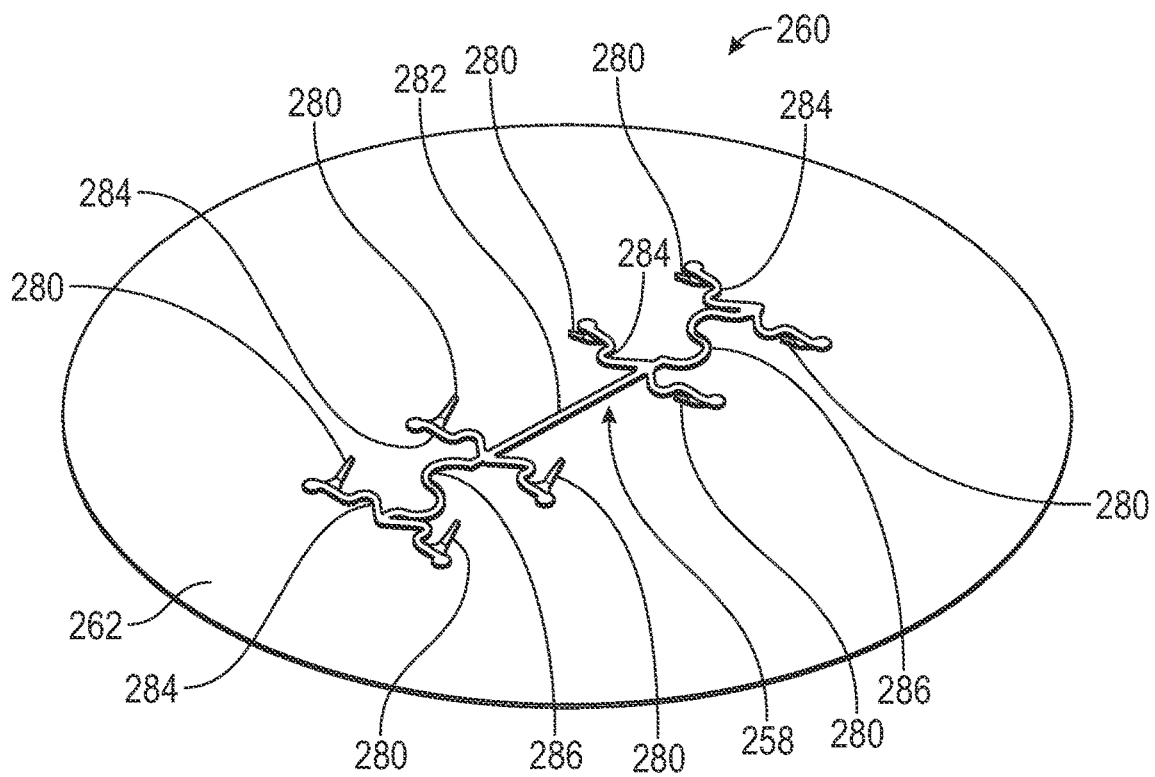
FIG. 24 is a perspective view of one of the microstructure devices of FIG. 23 showing a microstructure array configuration incorporating undulating struts.

FIG. 24 is a perspective view of microstructure device 260 of FIG. 23 showing microstructure array 258. Microstructure array 258 can comprise microstructures 280, bridge 282, spring structures 284 and spring structures 286. Bridge 282 can comprise a longitudinally straight strut connecting a plurality of microstructures 280 at each end thereof. Spring structures 286 can comprise undulating bodies extending distally from ends of bridge 282. Spring structures 284 can comprise undulating bodies extending transversely from ends of spring structures 286. Microstructures 280 can extend from transverse ends of spring structures 286. Spring structures 284 and 286 can provide microstructure device 260 with flexibility and conformability.

Microstructure devices 252A and 252B, microstructure device 260 and microstructure device 270 can comprise different configurations of devices that can be applied to the skin or tissue to treat, alleviate or prevent, pain. Microstructure devices 252A and 252B, microstructure device 260 and microstructure device 270 can have different shapes, skin footprints and microstructure footprints to engage different anatomy. Likewise, the depth or length of microstructures 280 can be configured to treat, alleviate or prevent pain. Furthermore, the density or spacing of microstructures 280 can be configured to treat pain.

Figure 25:
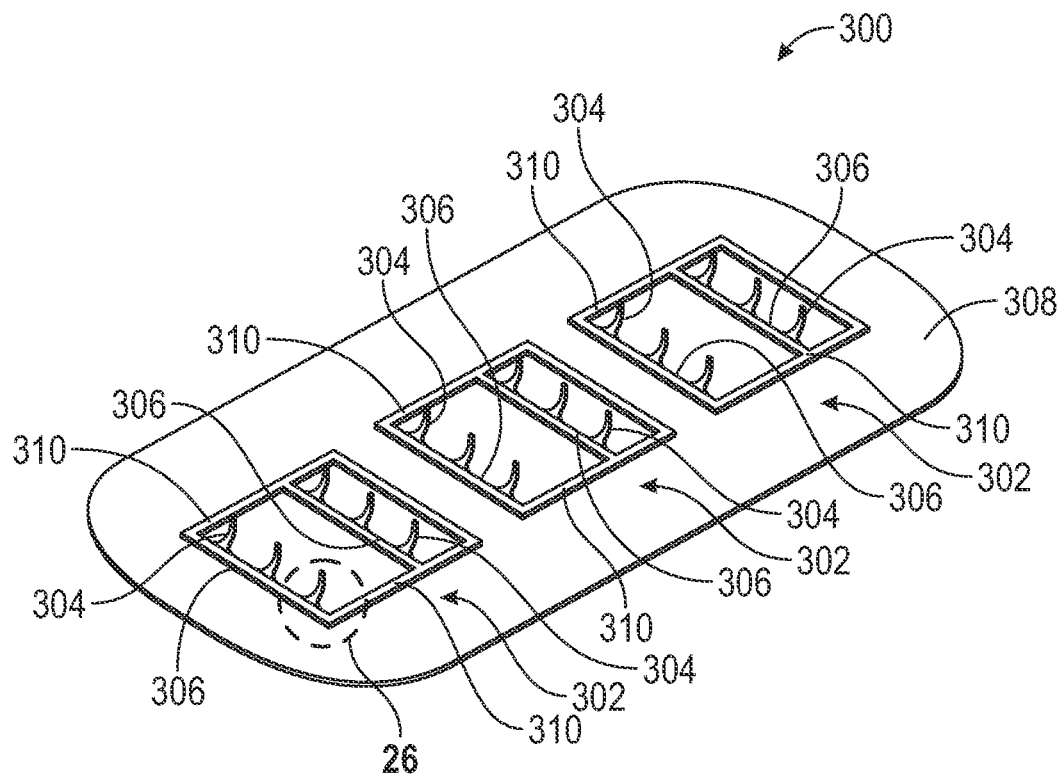
FIG. 25 is a perspective view of a microstructure device having a plurality of microstructure arrays including microstructures arranged along straight struts.
Figure 26:
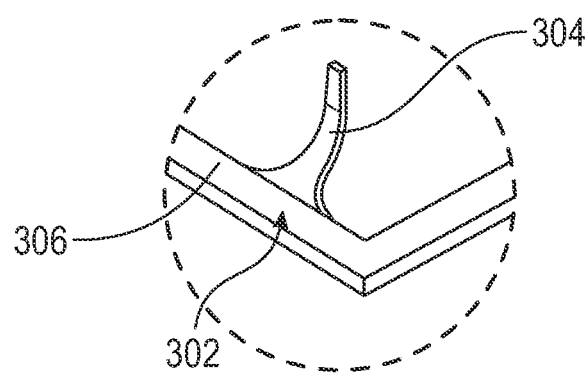
FIG. 26 is a perspective view of a microstructure of one of the microstructure arrays of FIG. 25.

FIG. 25 is a perspective view of microstructure device 300 having a plurality of microstructure arrays 302 including microstructures 304 arranged along straight struts 306. Microstructure arrays 302 can be coupled to backing 308. Straight struts 306 can be coupled to side struts 310 to form rectilinear foundations for microstructures 304. FIG. 26 is a perspective view of a microstructure 304 of one of the microstructure arrays 302 of FIG. 25. FIGS. 25 and 26 are discussed concurrently.

Backing 308 can be configured similarly to backing 54 of FIG. 5. Each of microstructure arrays 302 can be configured to position a plurality of microstructures 304 for engagement with skin. Struts 306 and side struts 310 can be connected in a rigid manner to allow microstructures 304 to penetrate into skin. Microstructures 304 can be spaced at intervals along struts 306 to provide densities commensurate with pain treatment described herein. Additionally, struts 306 can be spaced at intervals from each other to provide densities commensurate with pain treatment described herein. As such, the box-like framework of struts 306 and 310 can allow for configuring or tuning of microstructures 304 in spaced arrangements or densities that can facilitate pain treatment.

Micro-structures of the various devices described herein to relieve pain may be at fixed or variable distances from one another. The micro-structures should be at distances that have sufficient effects to relieve or prevent pain, but not so close together as to cause significant skin irritation. The distances from one another can range from 1 to 10 mm, 2 to 8 mm, 2 to 6 mm, 2 to 5 mm, 3 to 4 mm, or 3 mm. Preferably, the micro-structures are located at distances that are 2 to 5 mm apart and most preferably at 3 to 4 mm apart.

Ideally, the micro-structures can be applied over the area in which the pain is located or the area from which the pathology causing the pain originates. An example is application over the spinal area from which pain emanates that causes sciatica. The micro-structures can also be applied over both the area where the pain is located as well as the area from which the pain originates.

The particulars shown herein are by way of example and for purposes of illustrative discussion of the preferred embodiments of the present invention only, and they are presented in the cause of providing what is believed to be the most useful and readily understood description of the principles and conceptual aspects of various embodiments of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice.

Although our current studies have used microstructures that reach a depth of 1 mm in the skin, microstructures that are shorter (as short as 100 μm) or longer (up to 4 mm) may also be effective. The optimal range is from 500 μm to 1.5 mm in height of the microstructures (note: the total length may be longer than this if the microstructures are inserted into the skin at an angle; i.e. not perpendicular to the skin). The tip of the microstructures can be anywhere from 100 to 100,000 μm$^2$ in area. The optimal range is 1,000 to 10,000 μm$^2$ in area. The base can be a range of 100 to 1,000 μm in width or diameter of each microstructure.

The microstructures may be made of any suitable material or mixture of materials, and it may be any suitable width. In some embodiments, the base is made of any material or mixture of materials. In some embodiments the material is a polymer. In some embodiments, the material is a natural material, or a mixture of natural materials. In other embodiments, the material is a synthetic material, or a mixture of synthetic materials. In other embodiments, comprising mixtures of one or more synthetic materials and one or more natural materials. In particular embodiments, base are made of a material selected from a polymer, a metal, a biomaterial, and a combination thereof. In some embodiments, the base is comprised of or consists essentially of a metal. In some embodiments, the base is comprised of or consists essentially of a metal composite. In particular embodiments the base is comprised of or consists essentially of a metal or metal composite selected from the group consisting of: aluminum, titanium, stainless steel, magnesium and zinc. In some embodiments, the material is a series 300 stainless steel. In some embodiments, the material is 316 stainless steel.

The shape of the microstructures can be in the shape of blades, hooks, staples, needles, pyramids, cones, or other designs. Each individual microstructure can serve as a therapeutic modality or they can be placed together on a base to create an array of microstructures. The array can be in the shape of a square, rectangle, circle, pyramid, diamond, or other design. The microstructures in the array can be arranged along rows with identical spacing between rows or in staggered or any other non-identical spacing pattern.

The microstructures in the array can be at an angle of a range of 15 to 90 degrees with respect to the base of the array. Optimally, between 30 and 60 degrees, and ideally, at 45 degrees. The array can contain anywhere from 1 to 1.000 microstructures per cm$^2$. The size of the array can be anywhere from 1 to 10,000 cm$^2$ with an optimal range being between 2 and 250 cm$^2$. The array of microstructures may be flexible and/or elastic. The array may contain a spring component to allow elasticity and flexibility.

The array can be placed on an adhesive backing. In some embodiments, the backing is at least one of breathable, stretchable, flexible, and elastic. In some embodiments, the backing is at least one of permeable, semi-permeable, and impermeable. In some embodiments, the backing is at least one of transparent and opaque. The backing may be flexible and/or elastic. In some embodiments, the backing comprises at least one of medical tape, white cloth tape, surgical tape, tan cloth medical tape, silk surgical tape, clear tape, hypoallergenic tape, silicone, elastic silicone, polyurethane, elastic polyurethane, polyethylene, elastic polyethylene, rubber, latex, Gore-Tex, plastic, plastic components, polymer, biopolymer, woven material, non-woven material, and natural material. In some embodiments, the backing comprises a polyurethane-based film. In some embodiments, the backing has a shape comprising at least one of a circle, oval, ellipse, square, rectangle, triangle, diamond, butterfly, and hourglass.

In some embodiments, the backing is larger than the area of the microstructure arrays as shown in FIGS. 1-8 and 15-26. Thus, there is an area surrounding the arrays that contains backing with no microstructures. This design makes it easier to apply the device. It also reduces the risk of being stuck with microstructures either during application or removal. This can result in bleeding or infection. This is especially important if another person applies or removes the device as this will reduce the risk of transmitting infections from the patient to the person applying the device. The array may be placed in the center of the backing or off center.

In some embodiments, the device comprises a tab. In some embodiments, the device comprises a tab attached to the backing. In some embodiments, the device comprises a tab attached to the backing, wherein the tab configured to improve at least one of removing the device from its packaging and applying the device to the tissue. In some embodiments, the tab has a dimension at least as wide as the device. In some embodiments, the tab has a thickness of about 100 μm. In some embodiments, the tab comprises at least one of a metal, a plastic, and a foam.

Anywhere from one to 10,000 microstructures can be applied to the skin to treat the pain. Optimally, two to 1,000 microstructures are applied to the skin. Anywhere from one to 100 arrays can be applied to the skin. Optimally, two to 20 arrays are applied to the skin. Anywhere from one to 100 devices can be applied to the skin. Optimally two to 10 devices are applied to the skin. Individual microstructures can be placed at different depths in the skin in the same treated area.

FIGS. 1-8 and 15-26 provide examples of devices that incorporate microstructures for treatment of pain. Each microstructure has a height of approximately 1 mm. The individual microstructures are formed at angles with respect to the array so that they are able to securely anchor to the skin. In examples, the microstructures are incorporated into an array. In examples, the microstructures are separately mounted to devices. The array contains springs which enable movement of the device to reduce skin irritation. The device contains a backing which is stretchable and flexible to enable movement with the skin. The backing extends beyond the edges of the array in order to ease application and removal and reduce the risk of being stuck with microstructures which can lead to bleeding and infection. This could be either experienced by the patient or another individual applying or removing the device in which case transmission of infection could result.

The microstructures are to be inserted near the area of pain. Optimally, it should be place over the area containing pain. However, they can also be inserted as far away as 10 cm from the skin overlying the painful area. The insertion of the microstructures can be made with or without an applicator.

The microstructures can be worn on the skin from a range of one hour to 30 days with the optimal range being 2 to 7 days. This is achieved by placing the microstructures into an array that has an adhesive backing. Such a device is able to remain adherent to the skin for up to four weeks. Treatment can be given as often as every other day to once a month. Optimally, treatment is one to three times per week. Treatment can be at one or more painful sites.

Alternatively, treatment can be given as described above over a period of several weeks to months and then stopped. Pain relief can continue for an extended period of time lasting months to years after treatment has discontinued. This relief of chronic pain without the requirement of continued treatment may be related to the ability of treatment with the devices to break the cycle of chronic pain, which is thought to be due to a circuit in the central nervous system that results in pain continues after the original cause of the injury has primarily healed and resulting inflammation has dissipated. Treatment with the devices may disrupt or break this circuit resulting in relief of the chronic pain syndrome.

The shape and size of the microstructures as well as their density (number per cm$^2$) and number and size of arrays may vary depending on the medical condition, age and health of patient, location in the body where the microstructures are being inserted into the skin and the severity of the pain.

Microstructure Based Kit to Treat Pain

In some embodiments the devices of the present invention are provided as a system, which is a kit comprising at least one device, as described herein, and at least one other component that can optionally be used with the device e.g., to alleviate pain. Kits such as these may comprise one or more of the devices disclosed herein, as well as one or more other optional components such as, e.g., one or more covers (optionally comprising adhesive) to be applied over the device; one or more containers (e.g., bottles, pouches, packets, tubes) comprising a drug or therapeutic, cleansing and/or sterilization means (e.g., antiseptics, antibiotics, sterile saline), analgesics (e.g., Benzocaine or Lidocaine), which can optionally be applied to the skin prior to the application of the device; and instructions for using the devices. In other embodiments, the kit may include other analgesic agents or anti-inflammatory agents, such as non-steroidal drugs. The agents may be topical agents formulated in gels, ointments, creams, or solutions.

Clinical Applications

The microstructures of the invention may be used to treat, or provide relief of, any type of pain including, but not limited to, skin pain, subcutaneous tissue pain, interstitial tissue pain, back pain, pain in an extremity, arthralgia, muscle pain or myalgia, joint pain, inflammatory pain, arthritis pain, complex regional pain syndrome, lumbosacral pain, musculoskeletal pain, neuropathic pain, chronic pain, cancer-related pain, acute pain, postoperative pain, tendinitis, epicondylitis, arthritis, torn or partially torn or injured ligaments, torn or damaged meniscus, joint dislocation or damage, temporomandibular joint pain, bursitis, muscle overuse, pain due to reduced use of muscles, pain due to traumatic injury, acute muscle injury, muscle strain, muscle spasm, fracture, frozen shoulder, degenerative disc disease, spinal stenosis, rheumatoid arthritis, osteoarthritis, erosive osteoarthritis, psoriatic arthritis, juvenile rheumatoid arthritis, gout, pseudogout, axial spondyloarthritis, multiple sclerosis, allergic reactions, nephritic syndrome, scleroderma, thyroiditis, peripheral neuropathy, chemotherapy-related neuropathy, diabetic neuropathy, HIV related-neuropathy, fibromyalgia, radicular pain, sciatica, autoimmune conditions, acute vertebral crush fracture, fibrous dysplasia, SAPHO syndrome, osteoporosis, transient osteoporosis, or transient osteoporosis of the hip etc., interstitial cystitis, irritable bowel syndrome, chronic pelvic pain syndrome, Parkinson disease-related pain, post-stroke pain, endometriosis, migraine, cluster headache, and tension headache syndrome.

In some embodiments, the microstructure, may be used to treat, or provide relief of, any type of pain including, but not limited to, inflammatory pain, arthritis pain, myofascial pain, complex regional pain syndrome, lumbosacral pain, musculoskeletal pain, headache pain, neuropathic pain, chronic pain, cancer-related pain, acute pain, postoperative pain, visceral pain, pain of cardiac origin, kidney pain, bladder pain, chest pain, headaches, migraine headaches, post-herpetic neuralgia, fibromyalgia, etc.

With regard to treatment of the musculoskeletal system, the treatment of pain includes that related to the fibrous soft tissue including muscle and connective tissue layer. In various embodiments, the fibrous soft tissue can comprise any or all of the following tissues: a muscle, a tendon, a ligament, fascia, a sheath, cartilage, and an articular capsule. This includes myofascial pain (trigger points), trauma, arthritis, tendonitis, damaged or torn ligaments, damaged or torn tendons, bursitis, degenerative disc disease as well as many other musculoskeletal conditions. In addition to treating pain, the microstructure devices of the present disclosure can be used to prevent pain.

Treatment can be used on any region of the body including head, neck, back, face, chest, fingers, hands, wrists, arms, elbows, shoulders, buttocks, hips, thighs, knees, lower legs, ankles, feet, and toes. The pain may be of visceral origin and thus being experienced in the chest, abdominal, pelvic, or other regions of the body.

Treatment can be for mild, moderate, or severe pain. It can also be for pain that is chronic or acute. Treatment may be for pain that last a few hours to days while in other cases for pain that is of one or more years in duration. Treatment may be for recurrent, episodic, or sporadic pain. In some instances, pain relief may be palliative, or pain relief may be provided independent of improvement of the disease or condition or the underlying cause of the disease or condition. For example, although the underlying disease may not improve, or may continue to progress, an individual suffering from the disease may experience pain relief. Relief of pain may be transient or permanent. The invention may be used on humans or animals and is thus suitable for applications in veterinary medicine.

Treatment with microstructures can be combined with the treatment using other agents that alleviate pain, such as lidocaine, non-steroidal anti-inflammatory drugs, corticosteroids, opioids and counter irritants. These agents can be administered topically, systemically, or regionally. Treatment with microstructures is especially advantageous because it does not have the side effects of drugs and the other agents used to treat pain and there is thus no risk of increased toxicities by combination therapies. The microstructure treatment can also be combined with other physical treatments for pain including massage, electrical stimulation, ultrasound, massage, compression, heat, or ice to the painful area. The microstructure treatment can also be combined with therapeutic agents that target the underlying cause of the disease causing pain. These targets include cytokines, chemokines, inflammatory receptors, and other inflammatory mediators and pathways that cause inflammation or are contributing to the damage and pain caused by the disorder. These include antibodies, proteins, peptides, and small molecules.

The microstructure treatment can be used with muscle relaxants to relieve pain. The microstructure treatment can also be used with treatments that reduce anxiety or depression, conditions which can increase sensitivity to pain. The microstructures can also contain therapeutic agents, such as lidocaine, non-steroidal anti-inflammatory drugs, corticosteroids, or opioids. The microstructures can also be directly attached to a source of electrical current to provide electrical stimulation in combination with its direct effects to alleviate pain.

CLINICAL EXAMPLES

Insertion of microstructures into the skin near painful regions has been demonstrated to be effective in providing pain relief in a number of patients with a variety of conditions as described below. These patients were treated with microMend® devices (KitoTech Medical. Seattle. Wash.) consisting of arrays of microstructures attached to a backing that was the size and shape of a butterfly closure. Each device had two arrays of six microstructures that were approximately 1.5 mm in length and a height of about 1 mm and extended to a depth of approximately 1 mm into the skin. Devices were inserted into or near the area of skin overlying the painful site and remained on the skin for two to three days (FIGS. 9-14). In these case studies, pain upon insertion of the microstructure was either minimal or not felt by patients. In some cases, mild inflammation was observed at the sites of insertion, but disappeared a few days after removal of the devices. Pain was not reported by most patients while wearing the devices.

Example 1: Treatment of Osteoarthritis with Mirostaple Devices

Two microMend devices were applied to the right knee area (one above the joint and one below the joint—each approximately 5 cm from the area of pain) to a patient suffering from pain in this knee due to osteoarthritis (FIGS. 9-10). After one hour, pain subsided and was nearly absent by 24 hours after treatment. The devices remained in place for three days. The patient's pain was eliminated for over a week.

Two microMend devices were applied to the left elbow area in a patient suffering from pain in this elbow (FIGS. 11-12). After 24 hours, pain significantly subsided. The device remained in place for three days and pain was absent for approximately one week.

Example 2: Treatment of Sprain with Microstaple Device

Patient suffered an acute sprain of the left ankle associated with twisting his left foot while running. Pain was disabling such that the patient had trouble walking. Four microMend devices were applied into the skin over the left ankle. One day following application of the devices, the pain had substantially subsided such that the patient was able to walk more than a mile with minimal to no pain. The devices remained in place for four days. Pain continued to be reduced over the following weeks and has almost disappeared at three weeks.

Example 3: Treatment of Trigger Points

Patient suffered from recurrent bouts of myofascial pain (trigger points) in the lumbar area. After such a bout in the left lumbar region, two microMend devices were applied over the painful area. Pain was significantly reduced in one hour and was minimal at one day post-application. Devices were in place for a total of three days and pain continued to dissipate.

Example 4: Musculoskeletal Pain of Uncertain Etiology

A patient had pain for a duration of approximately one month in the right medial scapular region. Two devices were applied over the area, and pain was eliminated within one day. The microMend devices remained in place for a total of three days and there was no recurrence of pain for several weeks after applications of the devices.

Another patient had acute pain in the mid-thoracic area due to twisting of that region while performing work. Two microMend devices were applied to the area and remained in place for three days. Pain was significantly reduced by the treatment.

A third patient suffered from a few days of pain in the pretibial region of the right leg. One microMend device was placed over the painful area and the pain was markedly reduced by the next day and continued to be alleviated over the treatment period of 3 days.

Example 5

A patient suffering left lower lumbar musculoskeletal pain was treated with two devices for a period of three days. Two devices were also placed on the right lower lumbar area, where there was no pain. Inflammation of the skin manifested as mild redness and slight urticaria was observed and reported in the left lumbar but not the right lumbar area. The inflammatory symptoms in the left lumbar area disappeared within a few days of removing the devices. The fact that inflammation only occurred in the area of pain suggest that there may be some interaction between deeper musculoskeletal inflammation and the skin inflammatory response. This interaction could possibly enhance the pain relief achieved with microstructure treatment by possibly increasing counterirritant effects.

Example 6

A patient suffering from chronic low back pain and sciatica was treated with the devices placed on the lower lumbar area intermittently (approximately one to two times per month over a period of 6-8 months. The patient then received no further treatment, and has been pain free for more than three months after the last treatment.

Example 7

Devices containing microstructures in arrays on a backing for treatment of pain are shown in FIGS. 1-8. These devices contain microstructures incorporated into arrays that have springs to allow movement with the skin. The arrays are placed on a backing. The backing extends beyond the edges of the arrays.

Example Pain Devices

1. A device to reduce pain or inflammation comprising one or more microstructures.
2. A device according to Claim 1 that reduces pain.
3. A device according to Claim 1 that reduces inflammation.
4. The device of Claims 1-3, wherein the number of microstructures ranges from one to 1,000.
5. The device of Claims 1-3, wherein the number of microstructures ranges from two to 500.
6. The device of Claims 1-3, wherein the number of microstructures ranges from four to 100.
7. The device of Claims 1-3, wherein the number of microstructures ranges from six to 50.
8. The device of Claims 1-3, wherein the number of microstructures ranges from eight to 25.
9. The device of Claims 1-3, wherein the number of microstructures ranges from one to 10.
10. The device of Claims 1-3, wherein the number of microstructures comprised on the device is 2.
11. The device of Claims 1-3, wherein the number of microstructures comprised on the device is 4.
12. The device of Claims 1-3, wherein the number of microstructures comprised on the device is 6.
13. The device of Claim 1-3, wherein the number of microstructures comprised on the device is 10.
14. The device of Claims 1-3, wherein the number of microstructures comprised on the device is 25.
15. The device of Claims 1-3, wherein the number of microstructures comprised on the device is 50.
16. The device of Claims 1-3, wherein the number of microstructures comprised on the device is 100.
17. The device of any one of Claims 1-16, wherein at least one microstructure is capable of penetrating into tissue.
18. The device of Claim 17, wherein the tissue is skin.
19. The device of any one of Claims 1-18, wherein at least one microstructure is capable of holding tissue in place by grasping.
20. The device of Claims 1-3, wherein the microstructures are contained in an array of microstructures.
21. The device of Claim 20, wherein the one or more microstructure arrays are attached to a backing.
22. The device of Claim 21, wherein the backing is also flexible.
23. The device of Claim 22 wherein the flexible backing is also stretchable.
24. The device of Claim 22, wherein a portion of the flexible backing has a stiffness greater than other portions of the device.
25. The device of Claim 233, wherein the stretchable backing comprises elasticity.
26. The device of Claim 25, wherein the elastic properties of the device vary along or across the device.
27. The device of Claim 22, wherein the flexible backing is not stretchable.
28. The device of Claim 21, wherein the backing comprises adhesive.
29. The device of Claim 28, wherein the adhesive binds the one or more microstructure arrays to the backing.
30. The device of Claim 28, wherein the adhesive binds to skin and assists in the application of the device.
31. The device of Claim 28, wherein the adhesive is located on one or more tabs.
32. The device of Claim 31, wherein the adhesive tabs are removable.
33. The device of Claim 32, wherein removal of the adhesive tabs prevents or reduces the severity of adhesive-induced allergic responses.
34. The device of Claim 28, wherein the adhesive further assists in maintaining the device in its intended positioning on the skin.
35. The device of Claim 28, wherein the adhesive is an acrylate or hydrogel based adhesives that can stick to wet surfaces.
36. The device of Claim 28, wherein the adhesive is a polyethylene glycol (PEG) hydrogel adhesive.
37. The device of Claim 21, wherein the backing is made of a material selected from the group consisting of medical tape, white cloth tape, surgical tape, tan cloth medical tape, silk surgical tape, clear tape, hypoallergenic tape, silicone, elastic silicone, polyurethane, elastic polyurethane, polyethylene, elastic polyethylene, rubber, latex, Gore-Tex, plastic and plastic components, polymers, biopolymers, natural materials, and combinations thereof.
38. The device of Claim 21, wherein the backing is made of at least a portion of a commercially available product selected from the group consisting of 3M Transpore Surgical Tape, 3M Blenderm Surgical Tape, Coverlet Fabric. Dynarex Silk Surgical Tape. Kendall™ Hypoallergenic Clear Tape, Tenderfix™ Hypoallergenic Cloth Tape. Curasilk™ Cloth Tape, Curapont, Leukosan Skinlink, Leukosan Strip, Leukostrip, Steri-Strip, Steri-Strip S, Urgo strip, and combinations thereof.
39. The device of Claim 21, wherein the backing is in the form of a roll bandage.
40. The device of Claim 21, wherein two or more microstructure arrays are attached to a flexible backing such that they are separated by an isthmus.
41. The device of Claim 40, wherein the isthmus length ranges from 1-15 mm.
42. The device of Claim 40, wherein the isthmus is either the same width as the backing, narrower than the backing, or wider than the backing.
43. The device of Claim 40 wherein the isthmus width ranges from 2 mm-50 cm.
44. The device of Claim 1-3, further comprising a material selected from metal or polymer.
45. The device of Claim 19, wherein the microstructures are at an angle of from 15-90 degrees relative to the base or backing.
46. The device of Claim 19, wherein the microstructures of at least one array have an acute angle relative the flexible backing and the microstructures of at least one array are at a 90° angle relative to the base or backing.

47. The device of Claim 19, wherein the microstructures are at a variable angle relative to the base or backing depending on the position of the microstructures on the device.

48. The device of Claim 2, which further comprises a visual stress indicator on the flexible backing.

49. The device of Claim 48, wherein the stress indicator is a painted strip.

50. The device of Claims 1-3, wherein the microstructures are up to 100 μm long.

51. The device of Claims 1-3, wherein the microstructures are up to 200 μm long.

52. The device of Claim 1-3, wherein the microstructures are up to 500 μm long.

53. The device of Claims 1-3 wherein the microstructures are up to 700 μm long.

54. The device of Claim 1-3, wherein the microstructures are up to 1000 μm long.

55. The device of Claims 1-3, wherein the microstructures are up to 1500 μm long.

56. The device of Claims 1-3, wherein the microstructures are up to 2000 μm long.

57. The device of Claims 1-3, wherein the microstructures are up to 3000 μm long.

58. The device of Claims 1-3, wherein the microstructures are up to 500 μm wide where microneedle meets the foundation.

59. The device of Claims 1-3, wherein the microstructures are up to 1000 μm wide where it meets the foundation.

60. The closure device of Claims 1-3, wherein the microstructures are up to 2000 μm wide where it meets the foundation.

61. The device of Claims 1-3, wherein the microstructures are up to 3000 μm wide where it meets the foundation.

62. The device of Claims 1-3, wherein the microstructure comprise a tip width ranging from 1 μm to 1000 sm.

63. The device of Claims 1-3, wherein the microstructures comprise a tip diameter ranging from 1 μm to 100 μm.

64. The device of Claims 1-31, wherein the microstructures are in an array that comprises a number of microstructures that is less than a number selected from a group consisting of 1000, 500, 300, 100, 50, 25, 15, 10, 5, and 3.

65. The device of Claims 1-3, wherein the microstructures are in an array comprising from one to 100 microstructures per array.

66. The device of Claims 1-3, wherein the microstructures are in an array comprising from two to 20 microstructures per array.

67. The device of Claims 1-3, wherein the microstructures are in an array comprising from four to 10 microstructures per array.

68. The device of Claim 1, wherein the microstructures are in an array comprising at least two, three, four, five, or six microstructures per array.

69. The device of Claims 1-3, wherein the microstructures are in an array that comprises a number of microstructures per $cm^2$ that is less than a number selected from a group consisting of 1000, 500, 300, 100, 50, 25, 15, 10, 5, and 2.

70. The device of Claims 1-3, wherein the device has an area that is less than an area selected from the group consisting of 0.5 $cm^2$, 1 $cm^2$, 2 cm2, 3 $cm^2$, 4 $cm^2$, 6 $cm^2$, 8 $cm^2$, 10 $cm^2$, 15 $cm^2$, 20 $cm^2$, 30 $cm^2$, 40 $cm^2$, 50 $cm^2$, 75 $cm^2$, 100 $cm^2$, 200 $cm^2$, 500 $cm^2$, 1,000 $cm^2$, 2,500 $cm^2$, and 5,000 $cm^2$.

71. The device of Claims 1-3, wherein each array comprises at least one, two, three, four, five, six, seven, eight, nine, 10, 20, 50, 100, or 200 microstructures per $cm^2$.

72. The device of Claims 1-3, wherein the microstructure is curved.

73. The device of Claims 1-3, wherein the microstructures are distributed uniformly throughout the array.

74. The device of Claims 1-3, wherein the microstructures are distributed anisotropically throughout the array.

75. The device of Claims 1-3, wherein the microstructures have distribution in the array that is staggered.

76. The device of Claims 1-3, wherein the height of the microstructures is between 10 μm and 4 mm.

77. The device of Claims 1-3, wherein the height of the microstructures is between 100 μm and 3 mm.

78. The device of Claims 1-3, wherein the height of the microstructures is between 250 μm and 2 mm.

79. The device of Claims 1-3, wherein the height of the microstructures is between 500 μm and 1.6 mm.

80. The device of Claims 1-3, wherein the height of the microstructures is about 1 mm.

81. The device of Claims 1-3, wherein the microstructures penetrates skin to a depth between 100 μm and 3 mm.

82. The device of Claims 1-3, wherein the microstructures penetrates skin to a depth between 200 μm and 2 mm.

83. The device of Claims 1-3, wherein the microstructures penetrates skin to a depth between 500 μm and 2 mm.

84. The device of Claims 1-3, wherein the microstructures penetrates skin to a depth between 0.75 μm and 1.5 mm.

85. The device of Claims 1-3, wherein the microstructures penetrates skin to a depth of about 1 mm.

86. The device of Claims 1-3, wherein the length of the microstructures is variable across and along the device.

87. The device of Claims 1-3, wherein said device is capable of being attached to the skin by using traction and grip of the microstructures on tissue.

88. The device of Claims 1-3, wherein after application to the tissue, said device is covered with a protective cover.

89. The device of Claim 88, wherein the cover comprises adhesive.

90. The device of Claim 88, wherein the cover does not comprise adhesive.

91. The device of Claim 88, wherein the cover comprises a material with an appearance selected from a group consisting of transparent, opaque, colored, or patterned.

92. The device of Claim 88, wherein the cover comprises edges that are fashioned in a manner selected from the group consisting of curved, straight, or a combination thereof.

93. The device of Claim 88, wherein the cover comprises rounded edges; and wherein such a cover induces less irritation to the tissue surrounding the device than does a similar cover comprising straight edges.

94. The device of Claim 88, wherein the protective cover comprises a material selected from a group consisting of medical tape, white cloth tape, surgical tape, tan cloth medical tape, silk surgical tape, clear tape, hypoallergenic tape), silicone, elastic silicone, polyurethane, elastic polyurethane, polyethylene, elastic polyethylene, gauze, gel, hydrogel, silk, chitin, chitosan, cellulose, alginate, foam, shrink wrap, sheets, and hydrocolloids.

95. The device of Claim 88, wherein the protective cover comprises a commercially available product selected from a group consisting of Brown Medical—Sealtight Shower Dressing Protection Patch; Smith & Nephew Coversite Composite Cover Dressing; Coloplast Comfeel Plus Hydrocolloid Clear Thin Dressing; Systagenix Nu-Derm Bordered Hydrocolloid Wound Dressing; 3M Tegaderm Hydrocolloid Dressing; Smith & Nephew Replicare Thin Hydrocolloid Dressing; Smith & Nephew Replicare Hydrocolloid Wound Dressing; Hollister Restore Sterile Hydrocolloid Dressing; Hollister Restore Hydrocolloid Dressing with Foam; Backing; Hollister Restore Plus Hydrocolloid Dressing with Tapered Edge; Kendall Polyskin II Transparent Dressing; Smith & Nephew AlgiSite M Calcium Alginate Dressing; Kendall Curasorb Calcium Alginate Dressing; Deroyal Kalginate Calcium Alginate Dressing; Smith & Nephew Cica-Care Silicone Gel Sheeting; Molnlycke Mepiform Safetac Self Adherent Dressing with Soft Silicone for Scar Reduction; Molnlycke Mepitel Safetac Transparent Wound Contact Layer; Smith & Nephew OpSite Flexifix Transparent Film Roll; Systagenix Select Bioclusive Transparent Wound Dressing; Systagenix Select Bioclusive Transparent Wound Dressing; 3M Tegaderm Transparent Dressing First Aid Style; 3M Tegaderm Clear Absorbent Acrylic Dressing; Hartmann Cosmopore Adhesive Wound Dressing; 3M Tegaderm Transparent Film Dressing with Border; Kendall Telfa Sterile Clear Wound Dressing; Smith & Nephew Allevyn Thin Gentle-Adhesive Polyurethane Dressing; and combination thereof.
96. The device of Claims 1-3, wherein the microstructures comprise a material selected from a group consisting of a polymer, a metal, a biomaterial, a glass, a hydrogel, and a combination thereof.
97. The device of Claims 1-3, wherein the microstructures comprise a material selected from a group consisting of silicone, chitin, polymethyl methacrylate (PMMA), and a combination thereof.
98. The device of Claims 1-3, wherein the microstructures are selected from microneedles, microblades, microanchors, microfishscale, micropillars, and microhairs.
99. The device of Claims 1-3, wherein the microstructures comprise a shape selected from a group consisting of a rod, cone, square, rectangle, pyramid, cylinder.
100. The device of Claims 1-3, wherein the microstructures are tapered, untapered, or partially tapered.
101. The device of Claims 1-3, wherein the microstructures comprise a tip that is symmetrical.
102. The device of Claims 1-3, wherein the microstructures comprise a tip that is not symmetrical.
103. The device of Claims 1-3, wherein the microstructures are beveled at the tip or along one or more of the sides extending down the length of the microstructure.
104. The device of Claims 1-3, wherein said device can be applied by hand without the use of an applicator.
105. The device of Claims 1-3, wherein said device can be applied with an applicator or instrument.
106. The device of Claims 1-3, wherein said device can be removed without the use of a tool or instrument.
107. The device of Claim 88, wherein said device can be removed simply by removing from the skin an adhesive cover that is affixed to the back of the device, thereby simultaneously removing the device and the cover.
108. The device of Claims 1-3, wherein the device does not induce erythema in the tissue.
109. The device of Claims 1-3, wherein the device does not induce edema in the tissue.
110. The device of Claims 1-3, wherein the device does not cause skin scarring.
111. The device of Claims 1-3, wherein the method of the affixing is executed by placing the device in the desired position with the tips of the microstructures being oriented in contact with the tissue to which the device is meant to be affixed; applying pressure to the back of the microstructure array by pushing down on the base or backing directly behind the microstructures so as to induce the insertion of the microstructures into the tissue.
112. The method of Claim 111, wherein the affixing is executed using a roll-on handheld dispenser.
113. The method of Claims 1-3, further comprising covering the device with a cover after application of the device.
114. The device of Claims 1-3, comprising a microstructure comprising a foundation adjacent to a base, a tip, and a body connecting the foundation to the tip.
115. The device of Claim 114, wherein a line extending from the tip perpendicular to the base passes through the foundation.
116. The device of Claim 114, wherein a line extending from the tip perpendicular to the base does not pass through the foundation.
117. The device of Claim 114, wherein an angle between the body and the base is a constant angle.
118. The device of Claim 114, wherein two or more different angles are formed between the body and the base between the foundation and the tip.
119. The device of Claim 114, wherein the body is articulated.
120. The device of Claim 105, wherein the body is curved.
121. The device of Claim 114, wherein the body comprises at least one concave surface.
122. The device of Claim 114, wherein the body comprises at least one convex surface.
123. The device of Claim 114, wherein the body comprises at least one concave surface and at least one convex surface.
124. The device of Claim 114, wherein the tip is selected from the group consisting of a microneedle and a microblade.
125. A device according to claim 20 that contains an array with spring characteristics.
126. A device according to claim 125 comprising: a microstructure array, the array comprising a plurality of microstructure portions connected by at least one bridge portion, each of the plurality of microstructure portions comprising at least one microstructure for securing the array to the skin or tissue, and at least one of the plurality of microstructure portions comprising at least one structure with spring characteristics.
127. A device according to Claims 1-3 that remains on the skin or tissue for one hour to one month.
128. A device according to Claims 1-3 that remains on the skin for 8 hours to two weeks.
129. A device according to Claims 1-3 that remains on the skin for one day to 10 days.
130. A device according to Claims 1-3 that remains on the skin for two days to one week.
131. A device according to Claims 1-3 that remains on the skin for two to five days.
132. A device according to Claims 1-3 that remain on the skin for three days.

133. A device according to Claims 1-3 that is applied within one to 10 cm of the painful area.
134. A device according to Claims 1-3 that is applied within two to five cm of the painful area.
135. A device according to Claims 1-3 that is applied directly over the painful area.
136. Devices according to Claims 1-3 in which a range of one to 100 devices are used to treat the pain.
137. Devices according to Claims 1-3 in which a range of one to 50 devices are used to treat the pain.
138. Devices according to Claims 1-3 in which a range of one to 20 devices are used to treat the pain.
139. Devices according to Claims 1-3 in which a range of one to 10 devices are used to treat the pain.
140. Devices according to Claim 1 in which a range of one to five devices are used to treat the pain.
141. Devices according to Claims 1-3 in which a range of two to four devices are used to treat the pain.
142. A device according to Claim 21 in which the backing is larger than the microstructure array.
143. A device according to Claim 21 in which the array is placed on the backing such that there is a range of 5 mm to 20 cm distance between the perimeter of the array and the perimeter of the backing.
144. A device according to Claim 21 in which the array is placed on the backing such that there is a range of 1 cm to 10 cm distance between the perimeter of the array and the perimeter of the backing.
145. A device according to Claim 21 in which the array is placed on the backing such that there is a range of 2 cm to 5 cm distance between the perimeter of the array and the perimeter of the backing.
146. A device according to Claim 21 in which the array is placed in the center of the backing.
147. A device according to Claim 21 in which the array is not placed in the center of the backing.
148. A device according to Claim 1 containing an array of microstructures of different sizes or shapes.
149. A device according to Claim 1 containing an array of microstructures of different densities in the array.
150. A device according to Claim 21 containing arrays of microstructures of different sizes or shapes.
151. A device according to Claim 21 in which the arrays of microstructures are of different densities in the arrays.
152. A kit according to Claim 1 containing more than one device.
153. A kit according to Claim 1 containing devices of different sizes or shapes.
154. A kit according to Claim 1 containing devices with microstructures of different sizes and shapes.

Example Therapeutic Devices

1. A device containing microstructures that pierce tissue to reduce pain or inflammation.
2. A device according to Claim 1 containing microstructures that pierce tissue to reduce pain.
3. A device according to Claim 1 containing microstructures that pierce tissue to reduce inflammation.
4. A device according to Claims 1-3 that pierces skin.
5. A device according to Claims 1-4 to treat, or provide relief of, any type of pain including, but not limited to, skin pain, subcutaneous tissue pain, back pain, pain in an extremity, arthralgia, muscle pain or myalgia, joint pain, inflammatory pain, arthritis pain, complex regional pain syndrome, lumbosacral pain, musculoskeletal pain, neuropathic pain, chronic pain, cancer-related pain, acute pain, postoperative pain, tendinitis, epicondylitis, arthritis, torn or partially torn or injured ligaments, torn or damaged meniscus, joint dislocation or damage, temporomandibular joint pain, bursitis, muscle overuse, pain due to reduced use of muscles and skeleton, pain due to traumatic injury, acute muscle injury, muscle strain, muscle spasm, fracture, frozen shoulder, degenerative disc disease, spinal stenosis, rheumatoid arthritis, osteoarthritis, erosive osteoarthritis, psoriatic arthritis, juvenile rheumatoid arthritis, gout, pseudogout, axial spondyloarthritis, multiple sclerosis, allergic reactions, nephritic syndrome, scleroderma, thyroiditis, peripheral neuropathy, chemotherapy-related neuropathy, diabetic neuropathy, HIV related-neuropathy, fibromyalgia, radicular pain, sciatica, autoimmune conditions, acute vertebral crush fracture, fibrous dysplasia, SAPHO syndrome, osteoporosis, transient osteoporosis, or transient osteoporosis of the hip etc., interstitial cystitis, irritable bowel syndrome, chronic pelvic pain syndrome, Parkinson disease-related pain, post-stroke pain, endometriosis, migraine, cluster headache, and tension headache syndrome.
6. A device according to Claims 1-4 to treat, or provide relief of, any type of pain including, but not limited to, inflammatory pain, arthritis pain, myofascial pain, complex regional pain syndrome, lumbosacral pain, musculoskeletal pain, headache pain, neuropathic pain, chronic pain, cancer-related pain, acute pain, postoperative pain, visceral pain, pain of cardiac origin, kidney pain, bladder pain, chest pain, headaches, migraine headaches, post-herpetic neuralgia, fibromyalgia, etc.
7. A device according to Claims 1-4 to treat a condition of the musculoskeletal system, the treatment of pain includes that related to the fibrous soft tissue including muscle and connective tissue layer. In various embodiments, the fibrous soft tissue can comprise any or all of the following tissues: a muscle, a tendon, a ligament, fascia, a joint, a bursa, a sheath, cartilage, and an articular capsule or meniscus.
8. A condition according to Claim 7 that is arthritis.
9. A condition according to Claim 8 where the arthritis comprises osteoarthritis, gout, ankylosing arthritis, psoriatic arthritis, rheumatoid arthritis, juvenile rheumatoid arthritis, infectious arthritis, and systemic lupus erythematosus.
10. A device according to Claim 7 to treat muscle pain.
11. A device according to Claim 10 to treat myofascial pain also known as trigger points.
12. A device according to Claim 11 comprising trigger points in the shoulder, back, neck, scapular region, buttocks, hip, thigh, and hamstring muscles.
13. A device according to Claim 11 comprising trigger points in the shoulder, back, neck, scapular region, buttocks, hip, thigh, and hamstring muscles.
14. A device according to Claim 7 to treat pain from an acute muscle injury.
15. A device according to Claim 7 to treat a sprain.
16. A device according to Claim 7 to treat strain or tear of a tendon.
17. A device according to Claim 7 to treat tendinitis.
18. A device according to Claim 17 to treat epicondylitis.
19. A device according to Claim 7 to treat bursitis.
20. A device according to Claim 7 to treat dislocation of a joint.

21. A device according to Claim 20 where the joint comprises, interphalangeal, metacarpal, metatarsal, hand, knee, wrist, elbow, knee, hip, shoulder, spinal, ankle, and feet.
22. A device according to Claim 20 to treat temporomandibular joint dislocation.
23. A device according to claim 7 where there is damage to a ligament, such as a tear.
24. A device according to Claims 1-4 to treat pain in a region of the body, including head, neck, back, face, chest, fingers, hands, wrists, arms, elbows, shoulders, buttocks, hips, thighs, knees, lower legs, ankles, feet, and toes.
25. A device according to Claims 1-4 to treat pain of visceral origin.
26. A device according to Claims 1-4 to treat pain in the spinal region.
27. A device according to Claim 24 to treat the lumbar region.
28. A device according to Claim 24 to treat the thoracic region.
29. A device according to Claim 24 to treat the cervical region.
30. A device according to Claim 24 to treat the knee.
31. A device according to Claims 1-4 to treat pain that is mild, moderate or severe.
32. A device according to Claims 1-4 that is chronic.
33. A device according to Claims 1-4 that is acute.
34. A device according to Claims 1-4 to treat pain that is recurrent, episodic, or sporadic.
35. A device according to Claims 1-4 to provide pain relief that is independent of therapeutic effects on the underlying cause of the disease of condition.
36. A device according to Claims 1-4 where pain relief is transient.
37. A device according to Claims 1-4 where pain relief is permanent.
38. A device according to Claims 1-4 that can be used to treat humans.
39. A device according to Claims 1-4 that can be used to treat animals.
40. A device according to Claims 1-4 that can be used in combination with a treatment using other agents that alleviate pain, such as lidocaine, non-steroidal anti-inflammatory drugs, corticosteroids, opioids and counter irritants.
41. A device according to Claims 1-4 that can be combined with therapeutic agents that are administered topically, systemically, or regionally.
42. A device according to Claims 1-4 that can be combined with other physical treatments for pain including massage, electrical stimulation, ultrasound, massage, compression, heat, or ice to the painful area.
43. A device according to Claims 1-4 that can be combined with therapeutic agents that target the underlying cause of the disease causing pain.
44. A device according to Claims 1-4 that includes causes related to cytokines, chemokines, inflammatory receptors, and other inflammatory mediators and pathways that cause inflammation or are contributing to the damage and pain caused by the disorder.
45. A device according to Claim 44 that includes therapeutic agents, such as antibodies, proteins, peptides, and small molecules.
46. A device according to Claim 7 that can be used with muscle relaxants.
47. A device according to Claims 1-4 where it is combined with treatments for anxiety or depression, conditions which can increase pain sensitivities.
48. A device according to Claims 1-4 that contains therapeutic agents including therapeutic agents, such as lidocaine, non-steroidal anti-inflammatory drugs, corticosteroids, or opioids.
49. A device according to Claims 1-4 directly attached to a source of electrical current to alleviate pain.
50. A device according to Claims 1-4 included in a kit that may include other analgesic agents or anti-inflammatory agents, such as non-steroidal drugs.
51. A kit according to Claim 50, wherein the agents may be topical agents formulated in gels, ointments, creams, or solutions.
52. A device according to Claims 1-4 that relieves pain for one day to one year.
53. A device according to Claims 1-4 that relieves pain for one day to one month.
54. A device according to Claims 1-4 that relieves pain for two days to two weeks.
55. A device according to Claims 1-4 that relieves pain for three days to one week.
56. Devices according to Claims 1-4 that are used to relieve pain at more than one site.
57. A device according to Claims 1-4 in which treatment is continued for one day to one year and then discontinued, whereby the patient remains pain-free for a period of one week to several years.
58. A device according to Claims 1-4 in which treatment is continued for one month to one year and then discontinued, whereby the patient remains pain-free for a period of one week to several years.
59. A device according to Claims 1-4 in which treatment is continued for one day to one year and then discontinued, whereby the patient remains pain-free for a period of one month to several years.
60. A device according to Claims 1-4 in which treatment is continued for one month to one year and then discontinued, whereby the patient remains pain-free for a period of one month to several years.
61. A device according to Claims 1-4 in which treatment is continued for one day to one year and then discontinued, whereby the patient remains pain-free for a period of 3 months to several years.
62. A device according to Claims 1-4 in which treatment is continued for one month to one year and then discontinued, whereby the patient remains pain-free for a period of 3 months to several years.
63. A device according to Claims 1-4 in which treatment is continued for one day to one year and then discontinued, whereby the patient remains pain-free for a period of 3 months to one year.
64. A device according to Claims 1-4 in which treatment is continued for one month to one year and then discontinued, whereby the patient remains pain-free for a period of 3 months to one year.

The invention claimed is:
1. A method of reducing or preventing pain or inflammation using a device comprising:
a foundation interconnecting a plurality of spring structures;
a backing including an adhesive layer, the foundation affixed to the backing; and
a plurality of microstructures arrayed on the foundation, each microstructure of the plurality of microstructures extending from the foundation adjacent to a spring structure of the plurality of spring structures;

the method comprising:

applying the device to tissue in a lower back area to treat sciatica pain; and penetrating each microstructure of the plurality of microstructures into the tissue.

2. The method according to claim 1, wherein the microstructure device remains on the skin for a period of time selected from the following periods of time:

one day to 10 days;
1 hour to 10 days;
8 hours to 6 days; and
one day to 5 days.

3. The method according to claim 1, wherein the microstructure device is applied over an area of a pathology that is causing the pain.

4. The method according to claim 1, wherein applying the microstructure device to tissue comprises applying a plurality of microstructure devices in a range of two to 20 devices to treat the pain.

5. A device to reduce or prevent pain or inflammation, the device comprising:

a backing including an adhesive layer;

a plurality of circular base structures arrayed on the backing; and a plurality of microstructures, each microstructure of the plurality of microstructure extending from a circular base structure of the plurality of circular base structures, wherein the plurality of circular base structures are arrayed on the backing in multiple staggered lines.

6. The device of claim 5, wherein the plurality of circular base structures are arrayed on the backing in at least two parallel rows.

7. The device of claim 5, wherein each microstructure of the plurality of microstructures extends from a spring structure coupled to each corresponding circular base structure of the plurality of circular base structures.

* * * * *